US007115395B2

(12) United States Patent
Lovenberg et al.

(10) Patent No.: US 7,115,395 B2
(45) Date of Patent: Oct. 3, 2006

(54) DNAS ENCODING GUINEA PIG HISTAMINE RECEPTORS OF THE H4 SUBTYPE

(75) Inventors: Timothy Lovenberg, San Diego, CA (US); Changlu Liu, San Diego, CA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 316 days.

(21) Appl. No.: 10/626,398

(22) Filed: Jul. 23, 2003

(65) Prior Publication Data

US 2005/0074841 A1 Apr. 7, 2005

Related U.S. Application Data

(62) Division of application No. 09/790,849, filed on Feb. 22, 2001, now abandoned.

(60) Provisional application No. 60/208,260, filed on May 31, 2000.

(51) Int. Cl.

| | |
|---|---|
| ***C12P 21/02*** | (2006.01) |
| ***C12N 5/16*** | (2006.01) |
| ***C12N 1/21*** | (2006.01) |
| ***C12N 15/63*** | (2006.01) |
| ***C07H 21/04*** | (2006.01) |

(52) U.S. Cl. .................. 435/69.1; 435/320.1; 435/325; 435/252.3; 435/254.11; 435/254.2; 536/23.5; 530/350

(58) Field of Classification Search ..................... None
See application file for complete search history.

(56) References Cited

U.S. PATENT DOCUMENTS

| | | | |
|---|---|---|---|
| 5,194,596 A | 3/1993 | Tischer et al. | 530/399 |
| 5,350,836 A | 9/1994 | Kopchick et al. | 530/399 |
| 5,817,480 A | 10/1998 | Murry et al. | 435/69.1 |
| 5,882,893 A | 3/1999 | Goodearl | 435/69.1 |
| 5,885,824 A | 3/1999 | Yamada et al. | 435/252.3 |
| 6,136,559 A | 10/2000 | Lovenberg et al. | 435/69.1 |
| 6,204,017 B1 | 3/2001 | Behan et al. | 435/69.1 |
| 2002/0132755 A1 | 9/2002 | Jenkinson et al. | 514/1 |

FOREIGN PATENT DOCUMENTS

| | | |
|---|---|---|
| WO | 00/22131 A2 | 4/2000 |
| WO | 01/25432 A2 | 4/2001 |
| WO | 01/85786 A2 | 11/2001 |

OTHER PUBLICATIONS

Arrang, J.M., et al., "Autoinhibition of brain histamine release mediated by a novel class (H3) of histamine receptor," *Nature (London)*, 1983, 302(5911), 832-837.

Clark, M.A., et al., "Guanine nucleotides and pertussis toxin reduce the affinity of histamine H3 receptors on AtT-20 cells," *Agents Actions*, 1993, 40(304), 129-134.

Clark, M.A., et al., "High affinity histamine H3 receptors regulate ACTH release by AtT-20 cells," *Eur. J. Pharmacol.*, 1992, 210(1), 31-35.

Gantz, I., et al., "Molecular cloning of a gene encoding the histamine H2 receptor," *Proc. Natl. Acad. Sci. USA*, 1991, 88(2), 429-433.

DeVos, C., "H1-receptor antagonists: effects on leukocytes, myth or reality," *Clin. Exp. Allergy*, 1999, 29(*Supp. 3*), 60-63.

Hill, S.J., et al., "International union of pharmacology. IXXX. Classification of histamine receptors," *Pharmacol. Rev.*, 1997, 49(3), 253-278.

Konig, M.L., et al., "Method for identifying ligands that bind to cloned Gs- or Gi- coupled receptors," *Mol. Cell. Neurosci.*, 1991, 2(4), 331-337.

Lovenberg, T.W., et al., "Cloning and functional expression of the human histamine $H_3$ receptor," *Molecular Pharmacology*, 1999, 55, 1101-1107.

Mikayama, T., et al., "Molecular cloning and functional expression of a cDNA encoding glycosylation-inhibiting factor," *Proc. Natl. Acad. Sci. USA*, 1993, 90, 10056-10060.

Pollard, H., et al., "A detailed autoradiographic mapping of histamine H3 receptors in rat brain areas," *Neuroscience (Oxford)*, 1993, 52(1), 169-189.

Yamashita, M., et al., "Expression cloning of a cDNA encoding the bovine histamine H1 receptor," *Proc. Natl. Acad. Sci., USA*, 1991, 88(24), 11515-11519.

Oda, T., et al., "Molecular cloning and characterization of a novel type of histamine receptor preferentially expressed in leukocytes," *J. of Biological Chem. USA*, 2000, 275 (47), 36781-36786.

Raible, D.G., et al., "Pharmacologic characterization of a novel histamine receptor on human eosinophils," *Am. J. Respir. Crit. Care Med.*, 1994, 149, 1506-1511.

Voet, et al., BioChem, *John Wiley & Sons*, 1990, 126-128.

Vukicevic, S., et al., "Induction of nephrogenic mesenchyme by osteogenic protein 1 (bond morphometric protein 7)," *Proceedings of the National Academies of Sciences USA*, 1996, 93, 9021-9026.

Alberts, B. et al. 1994. Molecular Biology of the Cell, $3^{rd}$ Edition. p. 4.

Kohler, G., et al. "Continuous Cultures of Fused Cells Secreting Antibody of Predefined Specificity," Nature, 1975, 256, 495-497.

Marshall, "Gene Therapy's Growing Pains," Science, 1995, 269, 1050-1055.

Orkin, S. H. et al., 1995. "Report and Recommendations of the Panel to Assess the NIH Investment in Research on Gene Therapy,".

Stratagene Catalog, 1991. p. 66.

Verma, I. M. et al., Nature, 1997, 389, 239-242.

*Primary Examiner*—Ruixiang Li
(74) *Attorney, Agent, or Firm*—Woodcock Washburn LLP

(57) ABSTRACT

DNAs encoding the mammalian histamine H4 receptors have been cloned and characterized. These recombinant molecules are capable of expressing biologically active histamine H4 receptor protein. The cDNA's have been expressed in recombinant host cells that produce active recombinant protein. The pharmacology of known histamine ligands is demonstrated. The recombinant protein may be purified from the recombinant host cells. In addition, recombinant host cells are utilized to establish methods to identify modulators of the receptor activity, and receptor modulators are identified.

9 Claims, 13 Drawing Sheets

Figure 1: Nucleic Acid coding sequence human histamine H4

ATGCCAGATACTAATAGCACAATCAATTTATCACTAAGCACTCGTGTTACTTTAGCATTT
TTTATGTCCTTAGTAGCTTTTGCTATAATGCTAGGAAATGCTTTGGTCATTTTAGCTTTTG
TGGTGGACAAAAACCTTAGACATCGAAGTAGTTATTTTTTTCTTAACTTGGCCATCTCTG
ACTTCTTTGTGGGTGTGATCTCCATTCCTTTGTACATCCCTCACACGCTGTTCGAATGGG
ATTTTGGAAAGGAAATCTGTGTATTTTGGCTCACTACTGACTATCTGTTATGTACAGCAT
CTGTATATAACATTGTCCTCATCAGCTATGATCGATACCTGTCAGTCTCAAATGCTGTGT
CTTATAGAACTCAACATACTGGGGTCTTGAAGATTGTTACTCTGATGGTGGCCGTTTGG
GTGCTGGCCTTCTTAGTGAATGGGCCAATGATTCTAGTTTCAGAGTCTTGGAAGGATGA
AGGTAGTGAATGTGAACCTGGATTTTTTTCGGAATGGTACATCCTTGCCATCACATCATT
CTTGGAATTCGTGATCCCAGTCATCTTAGTCGCTTATTTCAACATGAATATTTATTGGAG
CCTGTGGAAGCGTGATCATCTCAGTAGGTGCCAAAGCCATCCTGGACTGACTGCTGTCT
CTTCCAACATCTGTGGACACTCATTCAGAGGTAGACTATCTTCAAGGAGATCTCTTTCTG
CATCGACAGAAGTTCCTGCATCCTTTCATTCAGAGAGACAGAGGAGAAAGAGTAGTCTC
ATGTTTTCCTCAAGAACCAAGATGAATAGCAATACAATTGCTTCCAAAATGGGTTCCTT
CTCCCAATCAGATTCTGTAGCTCTTCACCAAAGGGAACATGTTGAACTGCTTAGAGCCA
GGAGATTAGCCAAGTCACTGGCCATTCTCTTAGGGGTTTTTGCTGTTTGCTGGGCTCCAT
ATTCTCTGTTCACAATTGTCCTTTCATTTTATTCCTCAGCAACAGGTCCTAAATCAGTTTG
GTATAGAATTGCATTTTGGCTTCAGTGGTTCAATTCCTTTGTCAATCCTCTTTTGTATCCA
TTGTGTCACAAGCGCTTTCAAAAGGCTTTCTTGAAAATATTTTGTATAAAAAAGCAACC
TCTACCATCACAACACAGTCGGTCAGTATCTTCTTAA

Figure 2: Amino acid sequence human histamine H4 receptor

Met Pro Asp Thr Asn Ser Thr Ile Asn Leu Ser Leu Ser Thr Arg Val Thr Leu
Ala Phe Phe Met Ser Leu Val Ala Phe Ala Ile Met Leu Gly Asn Ala Leu Val
Ile Leu Ala Phe Val Val Asp Lys Asn Leu Arg His Arg Ser Ser Tyr Phe Phe
Leu Asn Leu Ala Ile Ser Asp Phe Phe Val Gly Val Ile Ser Ile Pro Leu Tyr
Ile Pro His Thr Leu Phe Glu Trp Asp Phe Gly Lys Glu Ile Cys Val Phe Trp
Leu Thr Thr Asp Tyr Leu Leu Cys Thr Ala Ser Val Tyr Asn Ile Val Leu Ile
Ser Tyr Asp Arg Tyr Leu Ser Val Ser Asn Ala Val Ser Tyr Arg Thr Gln His
Thr Gly Val Leu Lys Ile Val Thr Leu Met Val Ala Val Trp Val Leu Ala Phe
Leu Val Asn Gly Pro Met Ile Leu Val Ser Glu Ser Trp Lys Asp Glu Gly Ser
Glu Cys Glu Pro Gly Phe Phe Ser Glu Trp Tyr Ile Leu Ala Ile Thr Ser Phe
Leu Glu Phe Val Ile Pro Val Ile Leu Val Ala Tyr Phe Asn Met Asn Ile Tyr
Trp Ser Leu Trp Lys Arg Asp His Leu Ser Arg Cys Gln Ser His Pro Gly Leu
Thr Ala Val Ser Ser Asn Ile Cys Gly His Ser Phe Arg Gly Arg Leu Ser Ser
Arg Arg Ser Leu Ser Ala Ser Thr Glu Val Pro Ala Ser Phe His Ser Glu Arg
Gln Arg Arg Lys Ser Ser Leu Met Phe Ser Ser Arg Thr Lys Met Asn Ser Asn
Thr Ile Ala Ser Lys Met Gly Ser Phe Ser Gln Ser Asp Ser Val Ala Leu His
Gln Arg Glu His Val Glu Leu Leu Arg Ala Arg Arg Leu Ala Lys Ser Leu Ala
Ile Leu Leu Gly Val Phe Ala Val Cys Trp Ala Pro Tyr Ser Leu Phe Thr Ile
Val Leu Ser Phe Tyr Ser Ser Ala Thr Gly Pro Lys Ser Val Trp Tyr Arg Ile
Ala Phe Trp Leu Gln Trp Phe Asn Ser Phe Val Asn Pro Leu Leu Tyr Pro Leu
Cys His Lys Arg Phe Gln Lys Ala Phe Leu Lys Ile Phe Cys Ile Lys Lys Gln
Pro Leu Pro Ser Gln His Ser Arg Ser Val Ser Ser

Figure 3: Tissue Distribution of human histamine H4 receptor
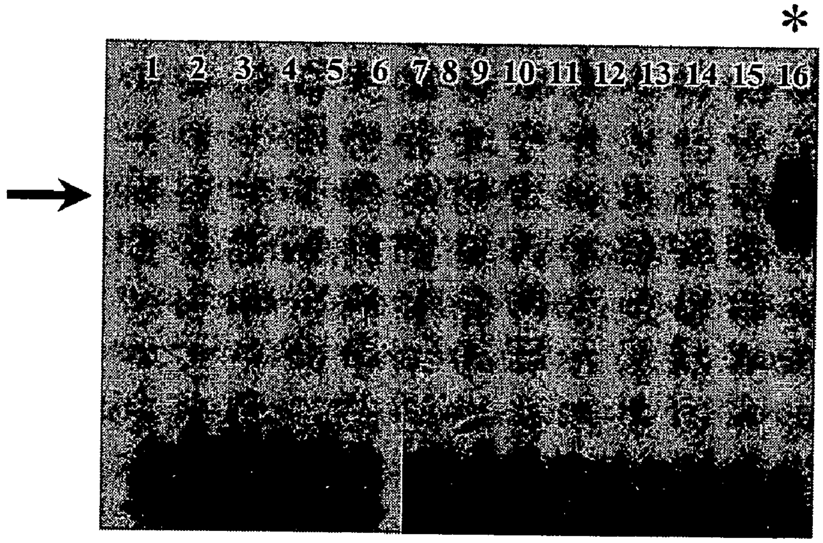
1 - Cerebellum
2 - Cortex
3 - Hypothalamus
4 - Small Intestine
5 - DRG
6 - Hippocampus
7 - Spleen
8 - Thalamus
9 - Placenta
10 - Heart
11 - Liver
12 - Lung
13 - Uterus
14 - Pituitary
15 - Spinal Cord
16 - Bone Marrow

Figure 4: Binding of [$^3$H]-histamine to pH4R expressing COS7 cells.
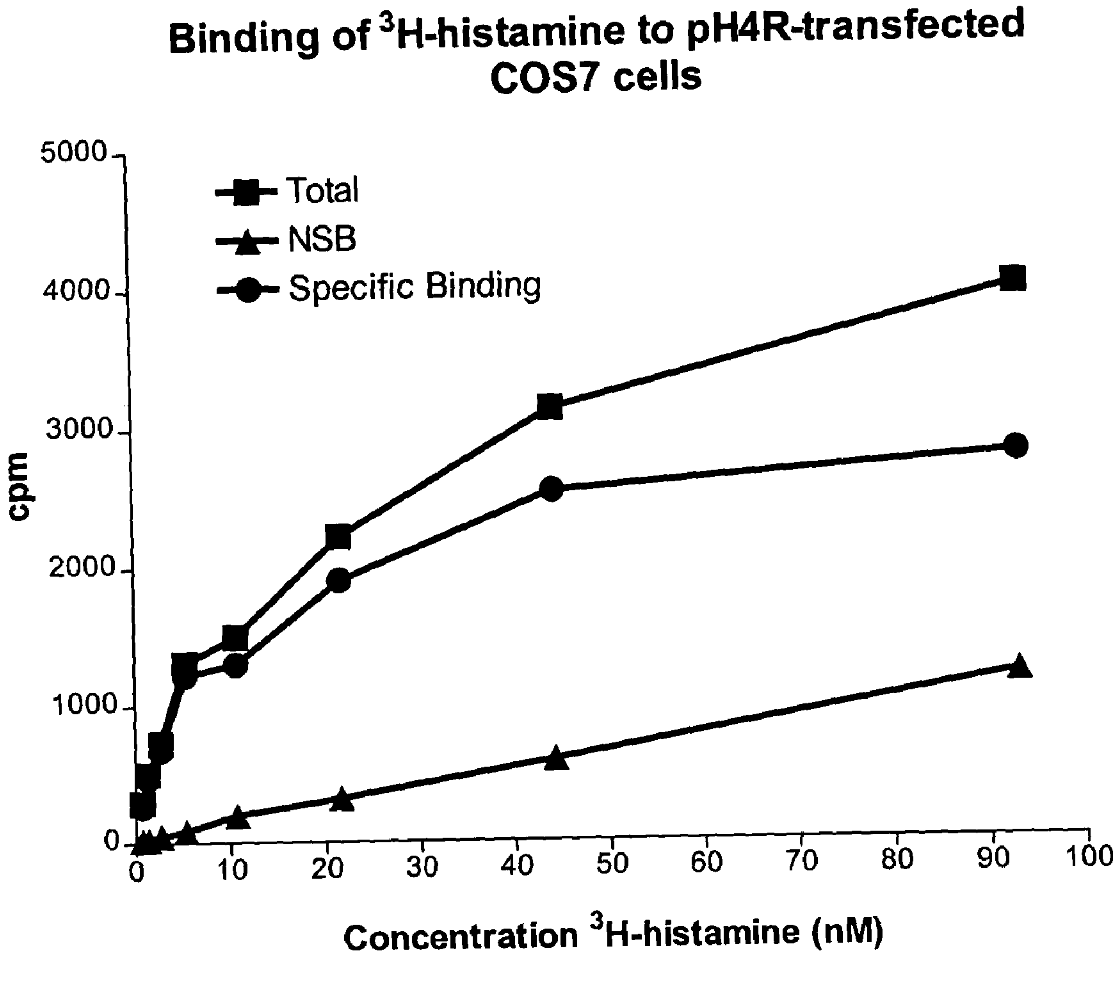

FIGURE 5A

Mouse H4 DNA coding region (SEQ.ID.NO.:5)

ATGTCGGAGTCTAACAGTACTGGCATCTTGCCACCAGCTGCTCAGGTCCCCTTGGCATTTTTAATGT
CTTCATTTGCCTTTGCTATAATGGTAGGCAATGCTGTGGTCATCTTAGCCTTTGTGGTGGACAGAAA
CCTTAGACATCGAAGTAATTATTTTTTTCTTAATTTGGCTATTTCTGACTTCCTCGTGGGTTTGATT
TCCATTCCTCTGTACATCCCTCACGTGTTGTTTAACTGGAATTTTGGAAGTGGAATCTGCATGTTTT
GGCTCATTACTGACTATCTTTTGTGCACCGCATCTGTCTACAATATTGTCCTCATTAGCTACGATCG
ATACCAGTCAGTTTCAAATGCTGTGTCTTATAGGGCTCAACACACTGGCATCATGAAGATTGTTGCT
CAAATGGTGGCTGTTTGGATACTGGCTTTCTTGGTAAATGGCCCGATGATTCTGGCTTCAGATTCTT
GGAAGAACAGCACGAACACAAAGGACTGTGAGCCTGGCTTTGTTACAGAGTGGTACATCCTCACCAT
TACAATGCTCTTGGAATTCCTGCTTCCTGTCATCTCTGTGGCTTATTTCAATGTACAGATTTACTGG
AGCCTGTGGAAGCGTAGGGCTCTCAGTAGGTGCCCTAGCCATGCTGGATTCTCCACTACCTCTTCCA
GTGCTTCAGGACACTTACACAGAGCTGGGGTGGCTTGCAGGACAAGTAATCCTGGATTGAAGGAATC
AGCTGCATCTCGTCACTCAGAAAGTCCTCGAAGAAAGAGCAGCATCCTGGTGTCCTTAAGGACTCAC
ATGAACAGCAGTATCACTGCCTTCAAAGTGGGTTCCTTCTGGCGATCGGAAAGTGCAGCGCTTCGCC
AAAGGGAGTACGCAGAGCTTCTCAGAGGCAGGAAGCTAGCCAGGTCACTGGCCATCCTTCTGAGCGC
TTTTGCCATTTGCTGGGCTCCATACTGTCTGTTCACAATTGTCCTTTCAACTTACCCCAGAACGGAA
CGCCCCAAATCGGTGTGGTACAGCATTGCCTTCTGGCTGCAATGGTTCAATTCGTTTGTTAATCCCT
TTCTGTACCCTTTGTGTCACAGGCGTTTCCAGAAGGCTTTCTGGAAGATACTTTGTGTGACAAAGCA
ACCAGCGCTGTCACAGAACCAGTCAGTATCTTCTTGA

FIGURE 5B

Rat H4 DNA coding region (SEQ.ID.NO.:6)

ATGTCGGAGTCTAACGGCACTGACGTCTTGCCACTGACTGCTCAAGTCCCCTTGGCATTTTTAATGT
CCCTGCTTGCTTTTGCTATAACGATAGGCAATGCTGTGGTCATTTTAGCCTTTGTAGCAGACAGAAA
CCTTAGACATCGAAGTAATTATTTTTTTCTTAATTTGGCTATTTCTGACTTCTTCGTGGGTGTCATC
TCCATTCCTCTGTACATCCCTCACACGCTGTTTAACTGGAATTTTGGAAGTGGAATCTGCATGTTTT
GGCTCATTACTGACTATCTTTTGTGCACAGCATCCGTCTACAGTATTGTCCTCATTAGCTACGATCG
ATACCAGTCAGTTTCAAACGCTGTGCGTTATAGAGCACAGCACACTGGCATCCTGAAAATTGTTGCT
CAAATGGTGGCTGTTTGGATACTGGCTTTCTTGGTCAATGGCCCAATGATTCTGGCTTCGGATTCTT
GGAAGAACAGCACCAACACAGAGGAGTGCGAGCCTGGCTTTGTTACTGAGTGGTACATCCTCGCCAT
TACAGCATTCTTGGAATTCCTGCTCCCTGTCTCCTTGGTGGTCTATTTCAGTGTACAGATTTACTGG
AGCCTGTGGAAGCGTGGGAGTCTCAGTAGGTGCCCTAGCCACGCTGGATTCATCGCTACCTCTTCCA
GGGGCACTGGACACTCACGCAGAACTGGGTTGGCTTGTAGGACAAGTCTTCCTGGATTAAAGGAACC
AGCCGCATCCCTTCATTCAGAAAGTCCACGAGGAAAGAGCAGTCTCCTGGTGTCCTTAAGGACTCAC
ATGAGCGGTAGTATCATCGCCTTCAAAGTGGGTTCCTTCTGCCGATCAGAAAGCCCAGTGCTTCACC
AGAGAGAGCACGTGGAGCTTCTCAGAGGCAGGAAGCTAGCCAGGTCGCTAGCTGTCCTCCTGAGTGC
TTTTGCCATTTGCTGGGCTCCGTATTGCCTGTTCACAATTGTTCTTTCAACTTATCGCAGAGGGGAG
CGCCCCAAATCGATTTGGTACAGCATAGCCTTTTGGCTACAGTGGTTCAATTCACTTATTAATCCCT
TTCTATACCCTTTGTGCCACAGACGTTTCCAGAAGGCTTTCTGGAAGATACTCTGTGTGACAAAGCA
ACCAGCACCTTCACAGACCCAGTCAGTATCTTCTTGA

FIGURE 5C

Guinea Pig H4 DNA coding sequence (SEQ.ID.NO.:7)

ATGTTGGCAAATAACAGTACAATCGCCTTAACATCAATTAAAATTTCTTTGACATTTTTA
ATGTCTTTACTAGCTATTGCTATAATGTTAGGCAATGTCGTGGTCATTTTAGCTTTTATTG
TGGACAGAAATCTTAGACATCGAAGTAATTACTTTTTTCTTAACTTGGCCATTGCAGACT
TCTTTGTGGGTGCAATTGCAATTCCTCTGTACATACCTTCCTCGCTGACTTACTGGACTT
CTGGAAAGCAAGCTTGTGTATTTTGGCTCATTACTGACTATCTTTTATGtACAGCATCTGT
GTATAATATTGTCCTCATCAGCTACGATCGCTACCAGTCAGTCTCAAATGCCGT GTGGTA
TAGAGCTCAGCACTCTGGCACCTGGAAAATTGCTACTCAGATGGTGGCTGTTTGGATAT
TCTCCTTCATGACAAATGGGCCGATGATTCTGATTTCAGACTCTTGGCAGAATAGCACT
ACAGAATGTGAACCTGGATTTTTAAAAAAGTGGTACTTTGCTCTCCCTACATCATTATTG
GAATTCCTGATCCCCATCTTGTTAGTTGCTTATTTCAGCGCCCATATTTACTGGAGCCTG
TGGAAGCGAGAGAAACTGAGCAGGTGCCTCAGCCACCCTGTACTCCCCTCTGACTCTTC
CAGCAGTGACCACGGACACTCCTGCAGACAGGACCCCGATTCAAGGGCGACTCTGCCA
GCACGGAAAGAAACAACTGCCTCTCTTGGTTCAGACAAGTCACGGAGAAAGAGCAGTC
TCTTGTTTTCCATAAGAGCCTACAAGAACAGCAATGTGATCGCTTCCAAAATGGGCTTC
CTCTCCCACTCAGATTCCCTGGCTCTTCAGCAAAGGGAACATATCGAACTTTTCAGAGC
CAGGAAATTAGCCAAGTCACTGGCCATACTCTTAGCAGCTTTTGCCATTTGCTGGGCTCC
ATATTCACTGACTACAGTTATCTACTCATTTTTTCCTGAAAGGAACTTGACTAAATCAAC
CTGGTACCATACTGCCTTTTGGCTCCAGTGGTTCAATTCCTTTGTTAATCCCTTTTTGTAT
CCATTGTGTCACAAACGTTTTCAGAAGGCTTTCCTGAAAATACTTCCTGTGAGAAGGCA
ATCCACGCCACCACACAACCGCTCAATATCCACTTGA

FIGURE 6A

Mouse histamine H4 receptor protein sequence (SEQ.IN.NO.:8)

MSESNSTGILPPAAQVPLAFLMSSFAFAIMVGNAVVILAFVVDRNLRHRSNYFFLNLAISDFL
VGLISIPLYIPHVLFNWNFGSGICMFWLITDYLLCTASVYNIVLISYDRYQSVSNAVSYRAQH
TGIMKIVAQMVAVWILAFLVNGPMILASDSWKNSTNTKDCEPGFVTEWYILTITMLLEFLLP
VISVAYFNVQIYWSLWKRRALSRCPSHAGFSTTSSSASGHLHRAGVACRTSNPGLKESAASR
HSESPRRKSSILVSLRTHMNSSITAFKVGSFWRSESAALRQREYAELLRGRKLARSLAILLSA
FAICWAPYCLFTIVLSTYPRTERPKSVWYSIAFWLQWFNSFVNPFLYPLCHRRFQKAFWKIL
CVTKQPALSQNQSVSS

FIGURE 6B

Rat histamine H4 receptor protein sequence (SEQ.ID.NO.:9)

MSESNGTDVLPLTAQVPLAFLMSLLAFAITIGNAVVILAFVADRNLRHRSNYFFLNLAISDFF
VGVISIPLYIPHTLFNWNFGSGICMFWLITDYLLCTASVYSIVLISYDRYQSVSNAVRYRAQH
TGILKIVAQMVAVWILAFLVNGPMILASDSWKNSTNTEECEPGFVTEWYILAITAFLEFLLPV
SLVVYFSVQIYWSLWKRGSLSRCPSHAGFIATSSRGTGHSRRTGLACRTSLPGLKEPAASLH
SESPRGKSSLLVSLRTHMSGSIIAFKVGSFCRSESPVLHQREHVELLRGRKLARSLAVLLSAF
AICWAPYCLFTIVLSTYRRGERPKSIWYSIAFWLQWFNSLINPFLYPLCHRRFQKAFWKILCV
TKQPAPSQTQSVSS

FIGURE 6C

Guinea Pig histamine H4 receptor protein sequence (389 amino acids)

(SEQ.ID.NO.:10)

MLANNSTIALTSIKISLTFLMSLLAIAIMLGNVVVILAFIVDRNLRHRSNYFFLNLAIADFFVG
AIAIPLYIPSSLTYWTSGKQACVFWLITDYLLCTASVYNIVLISYDRYQSVSNAVWYRAQHS
GTWKIATQMVAVWIFSFMTNGPMILISDSWQNSTTECEPGFLKKWYFALPTSLLEFLIPILLV
AYFSAHIYWSLWKREKLSRCLSHPVLPSDSSSSDHGHSCRQDPDSRATLPARKETTASLGSD
KSRRKSSLLFSIRAYKNSNVIASKMGFLSHSDSLALQQREHIELFRARKLAKSLAILLAAFAIC
WAPYSLTTVIYSFFPERNLTKSTWYHTAFWLQWFNSFVNPFLYPLCHKRFQKAFLKILPVRR
QSTPPHNRSIST

Figure 7A
Nucleotide Sequence Comparison of Human (SEQ ID NO:1), Guinea Pig (SEQ ID NO:7), Mouse (SEQ ID NO:5), and Rat H4 (SEQ ID NO:6)

```
      Human: ATGCCAGATACTAATAGCACAATCAATTTATCACTAAGCACTCGTGTTACTTTAGCATTTTTTATGTCCTTAGTAGCTTTTGCTATAATGCTAGGAAATGCTTTGGTCATTTTAGCTTTT 120
 Guinea Pig: ATGTTGGCAAATAACAGTACAATCGCCTTAACA---TCAATTAAAATTTCTTTGACATTTTTAATGTCTTTACTAGCTATTGCTATAATGTTAGGCAATGTCGTGGTCATTTTAGCTTTT 117
      Mouse: ATGTCGGAGTCTAACAGTACTGGCATCTTGCCACCAGCTGCTCAGGTCCCCTTGGCATTTTTAATGTCTTCATTTGCCTTTGCTATAATGGTAGGCAATGCTGTGGTCATCTTAGCCTTT 120
        Rat: ATGTCGGAGTCTAACGGCACTGACGTCTTGCCACTGACTGCTCAAGTCCCCTTGGCATTTTTAATGTCCCTGCTTGCTTTTGCTATAACGATAGGCAATGCTGTGGTCATTTTAGCCTTT 120

      Human: GTGGTGGACAAAAACCTTAGACATCGAAGTAGTTATTTTTTTCTTAACTTGGCCATCTCTGACTTCTTTGTGGGTGTGATCTCCATTCCTTTGTACATCCCTCACACGCTGTTCGAATGG 240
 Guinea Pig: ATTGTGGACAGAAATCTTAGACATCGAAGTAATTACTTTTTTCTTAACTTGGCCATTGCAGACTTCTTTGTGGGTGCAATTGCAATTCCTCTGTACATACCTTCCTCGCTGACTTACTGG 237
      Mouse: GTGGTGGACAGAAACCTTAGACATCGAAGTAATTATTTTTTTCTTAATTTGGCTATTTCTGACTTCCTCGTGGGTTTGATTTCCATTCCTCTGTACATCCCTCACGTGTTGTTTAACTGG 240
        Rat: GTAGCAGACAGAAACCTTAGACATCGAAGTAATTATTTTTTTCTTAATTTGGCTATTTCTGACTTCTTCGTGGGTGTCATCTCCATTCCTCTGTACATCCCTCACACGCTGTTTAACTGG 240

      Human: GATTTTGGAAAGGAAATCTGTGTATTTTGGCTCACTACTGACTATCTGTTATGTACAGCATCTGTATATAACATTGTCCTCATCAGCTATGATCGATACCTGTCAGTCTCAAATGCTGTG 360
 Guinea Pig: ACTTCTGGAAAGCAAGCTTGTGTATTTTGGCTCATTACTGACTATCTTTTATGtACAGCATCTGTGTATAATATTGTCCTCATCAGCTACGATCGCTACCAGTCAGTCTCAAATGCCGTG 357
      Mouse: AATTTTGGAAGTGGAATCTGCATGTTTTGGCTCATTACTGACTATCTTTTGTGCACCGCATCTGTCTACAATATTGTCCTCATTAGCTACGATCGATACCAGTCAGTTTCAAATGCTGTG 360
        Rat: AATTTTGGAAGTGGAATCTGCATGTTTTGGCTCATTACTGACTATCTTTTGTGCACAGCATCCGTCTACAGTATTGTCCTCATTAGCTACGATCGATACCAGTCAGTTTCAAACGCTGTG 360

      Human: TCTTATAGAACTCAACATACTGGGGTCTTGAAGATTGTTACTCTGATGGTGGCCGTTTGGGTGCTGGCCTTCTTAGTGAATGGGCCAATGATTCTAGTTTCAGAGTCTTGGAAGGATGAA 480
 Guinea Pig: TGGTATAGAGCTCAGCACTCTGGCACCTGGAAAATTGCTACTCAGATGGTGGCTGTTTGGATATTCTCCTTCATGACAAATGGGCCGATGATTCTGATTTCAGACTCTTGGCAGAATAGC 477
      Mouse: TCTTATAGGGCTCAACACACTGGCATCATGAAGATTGTTGCTCAAATGGTGGCTGTTTGGATACTGGCTTTCTTGGTAAATGGCCCGATGATTCTGGCTTCAGATTCTTGGAAGAACAGC 480
        Rat: CGTTATAGAGCACAGCACACTGGCATCCTGAAAATTGTTGCTCAAATGGTGGCTGTTTGGATACTGGCTTTCTTGGTCAATGGCCCAATGATTCTGGCTTCGGATTCTTGGAAGAACAGC 480

      Human: GGT---AGT---GAATGTGAACCTGGATTTTTTTCGGAATGGTACATCCTTGCCATCACATCATTCTTGGAATTCGTGATCCCAGTCATCTTAGTCGCTTATTTCAACATGAATATTTAT 594
 Guinea Pig: ACT---ACA---GAATGTGAACCTGGATTTTTAAAAAAGTGGTACTTTGCTCTCCCTACATCATTATTGGAATTCCTGATCCCCATCTTGTTAGTTGCTTATTTCAGCGCCCATATTTAC 591
      Mouse: ACGAACACAAAGGACTGTGAGCCTGGCTTTGTTACAGAGTGGTACATCCTCACCATTACAATGCTCTTGGAATTCCTGCTTCCTGTCATCTCTGTGGCTTATTTCAATGTACAGATTTAC 600
        Rat: ACCAACACAGAGGAGTGCGAGCCTGGCTTTGTTACTGAGTGGTACATCCTCGCCATTACAGCATTCTTGGAATTCCTGCTCCCTGTCTCCTTGGTGGTCTATTTCAGTGTACAGATTTAC 600

      Human: TGGAGCCTGTGGAAGCGTGATCATCTCAGTAGGTGCCAAAGCCATCCTGGACTG---ACTGCTGTCTCTTCCAACATCTGTGGACACTCATTCAGAGGTAGACTATCTTCAAGGAGATCT 711
 Guinea Pig: TGGAGCCTGTGGAAGCGAGAGAAACTGAGCAGGTGCCTCAGCCACCCTGTACTCCCCTCTGACTCTTCCAGCAGTGACCACGGACACTCCTGCAGACAGGACCCCGATTCAAGGGCGACT 711
      Mouse: TGGAGCCTGTGGAAGCGTAGGGCTCTCAGTAGGTGCCCTAGCCATGCTGGATTC---TCCACTACCTCTTCCAGTGCTTCAGGACACTTACACAGAGCTGGGGTGGCTTGCAGGACAAGT 717
        Rat: TGGAGCCTGTGGAAGCGTGGGAGTCTCAGTAGGTGCCCTAGCCACGCTGGATTC---ATCGCTACCTCTTCCAGGGGCACTGGACACTCACGCAGAACTGGGTTGGCTTGTAGGACAAGT 717

      Human: CTTTCTGCATCGACAGAAGTTCCTGCATCCTTTCATTCAGAGAGACAGAGGAGAAAGAGTAGTCTCATGTTTTCCTCAAGAACCAAGATGAATAGCAATACAATTGCTTCCAAAATGGGT 831
 Guinea Pig: CTGCCAGCACGGAAAGAAACAACTGCCTCTCTTGGTTCAGACAAGTCACGGAGAAAGAGCAGTCTCTTGTTTTCCATAAGAGCCTACAAGAACAGCAATGTGATCGCTTCCAAAATGGGC 831
      Mouse: AATCCTGGATTGAAGGAATCAGCTGCATCTCGTCACTCAGAAAGTCCTCGAAGAAAGAGCAGCATCCTGGTGTCCTTAAGGACTCACATGAACAGCAGTATCACTGCCTTCAAAGTGGGT 837
        Rat: CTTCCTGGATTAAAGGAACCAGCCGCATCCCTTCATTCAGAAAGTCCACGAGGAAAGAGCAGTCTCCTGGTGTCCTTAAGGACTCACATGAGCGGTAGTATCATCGCCTTCAAAGTGGGT 837

      Human: TCCTTCTCCCAATCAGATTCTGTAGCTCTTCACCAAAGGGAACATGTTGAACTGCTTAGAGCCAGGAGATTAGCCAAGTCACTGGCCATTCTCTTAGGGGTTTTGCTGTTTGCTGGGCT 951
 Guinea Pig: TTCCTCTCCCACTCAGATTCCCTGGCTCTTCAGCAAAGGGAACATATCGAACTTTTCAGAGCCAGGAAATTAGCCAAGTCACTGGCCATACTCTTAGCAGCTTTTGCCATTTGCTGGGCT 951
      Mouse: TCCTTCTGGCGATCGGAAAGTGCAGCGCTTCGCCAAAGGGAGTACGCAGAGCTTCTCAGAGGCAGGAAGCTAGCCAGGTCACTGGCCATCCTTCTGAGCGCTTTTGCCATTTGCTGGGCT 957
        Rat: TCCTTCTGCCGATCAGAAAGCCCAGTGCTTCACCAGAGAGAGCACGTGGAGCTTCTCAGAGGCAGGAAGCTAGCCAGGTCGCTAGCTGTCCTCCTGAGTGCTTTTGCCATTTGCTGGGCT 957
```

Figure 7B

```
     Human: CCATATTCTCTGTTCACAATTGTCCTTTCATTTTATTCCTCAGCAACAGGTCCTAAATCAGTTTGGTATAGAATTGCATTTTGGCTTCAGTGGTTCAATTCCTTTGTCAATCCTCTTTTG 1071
Guinea Pig: CCATATTCACTGACTACAGTTATCTACTCATTTTTTCCTGAAAGGAACTTGACTAAATCAACCTGGTACCATACTGCCTTTTGGCTCCAGTGGTTCAATTCCTTTGTTAATCCCTTTTTG 1071
     Mouse: CCATACTGTCTGTTCACAATTGTCCTTTCAACTTACCCCAGAACGGAACGCCCCAAATCGGTGTGGTACAGCATTGCCTTCTGGCTGCAATGGTTCAATTCGTTTGTTAATCCCTTTCTG 1077
       Rat: CCGTATTGCCTGTTCACAATTGTTCTTTCAACTTATCGCAGAGGGGAGCGCCCCAAATCGATTTGGTACAGCATAGCCTTTTGGCTACAGTGGTTCAATTCACTTATTAATCCCTTTCTA 1077

     Human: TATCCATTGTGTCACAAGCGCTTTCAAAAGGCTTTCTTGAAAATATTTTGTATAAAAAAGCAACCTCTACCATCACAACACAGTCGGTCAGTATCTTCTTAA                1173
Guinea Pig: TATCCATTGTGTCACAAACGTTTTCAGAAGGCTTTCCTGAAAATACTTCCTGTGAGAAGGCAATCCACGCCACCA---CACAACCGCTCAATATCCACTTGA                1170
     Mouse: TACCCTTTGTGTCACAGGCGTTTCCAGAAGGCTTTCTGGAAGATACTTTGTGTGACAAAGCAACCAGCGCTGTCA---CAGAACCAGTCAGTATCTTCTTGA                1176
       Rat: TACCCTTTGTGCCACAGACGTTTCCAGAAGGCTTTCTGGAAGATACTCTGTGTGACAAAGCAACCAGCACCTTCA---CAGACCCAGTCAGTATCTTCTTGA                1176
```

Figure 8

Amino Acid sequence Comparison of Human (SEQ ID NO:2), Guinea Pig (SEQ ID NO:10), Mouse (SEQ ID NO:8) and Rat H4 (SEQ ID NO:9)

```
      Human: MPDTNSTINLSLSTRVTLAFFMSLVAFAIMLGNALVILAFVVDKNLRHRSSYFFLNLAISDFFVGVISIPLYIPHTLFEWDFGKEICVFWLTTDYLLCTA 100
 Guinea Pig: MLANNSTIALT-SIKISLTFLMSLLAIAIMLGNVVVILAFIVDRNLRHRSNYFFLNLAIADFFVGAIAIPLYIPSSLTYWTSGKQACVFWLITDYLLCTA 99
      Mouse: MSESNSTGILPPAAQVPLAFLMSSFAFAIMVGNAVVILAFVVDRNLRHRSNYFFLNLAISDFLVGLISIPLYIPHVLFNWNFGSGICMFWLITDYLLCTA 100
        Rat: MSESNGTDVLPLTAQVPLAFLMSLLAFAITIGNAVVILAFVADRNLRHRSNYFFLNLAISDFFVGVISIPLYIPHTLFNWNFGSGICMFWLITDYLLCTA 100
  Consensus: M ..N.T .L: :.:::L:F:MSL:A:AIM:GN.:VILAF::D:NLRHRS:YFFLNLAI:DF:VG.I:IPLYIP.:L  W. G : C:FWL.TDYLLCTA
                                        TM1                                   TM2                     TM3

      Human: SVYNIVLISYDRYLSVSNAVSYRTQHTGVLKIVTLMVAVWVLAFLVNGPMILVSESWKDEG-S-ECEPGFFSEWYILAITSFLEFVIPVILVAYFNMNIY 198
 Guinea Pig: SVYNIVLISYDRYQSVSNAVWYRAQHSGTWKIATQMVAVWIFSFMTNGPMILISDSWQNST-T-ECEPGFLKKWYFALPTSLLEFLIPILLVAYFSAHIY 197
      Mouse: SVYNIVLISYDRYQSVSNAVSYRAQHTGIMKIVAQMVAVWILAFLVNGPMILASDSWKNSTNTKDCEPGFVTEWYILTITMLLEFLLPVISVAYFNVQIY 200
        Rat: SVYSIVLISYDRYQSVSNAVRYRAQHTGILKIVAQMVAVWILAFLVNGPMILASDSWKNSTNTEECEPGFVTEWYILAITAFLEFLLPVSLVVYFSVQIY 200
  Consensus: SVYNIVLISYDRY SVSNAV YR:QH:G. KI.. MVAVW:::F:.NGPMIL:S:SW::.. : :CEPGF:..WY:::.T.:LEF::P::.VAYF:.:IY
                                                     TM4                               TM5

      Human: WSLWKRDHLSRCQSHPGL-TAVSSNICGHSFRGRLSSRRSLSASTEVPASFHSERQRRKSSLMFSSRTKMNSNTIASKMGSFSQSDSVALHQREHVELLR 297
 Guinea Pig: WSLWKREKLSRCLSHPVLPSDSSSSDHGHSCRQDPDSRATLPARKETTASLGSDKSRRKSSLLFSIRAYKNSNVIASKMGFLSHSDSLALQQREHIELFR 297
      Mouse: WSLWKRRALSRCPSHAGF-STTSSSASGHLHRAGVACRTSNPGLKESAASRHSESPRRKSSILVSLRTHMNSSITAFKVGSFWRSESAALRQREYAELLR 299
        Rat: WSLWKRGSLSRCPSHAGF-IATSSRGTGHSRRTGLACRTSLPGLKEPAASLHSESPRGKSSLLVSLRTHMSGSIIAFKVGSFCRSESPVLHQIEHVELLR 299
  Consensus: WSLWKR:.LSRC SH. : :. SS.  GH. R   .:R :::...E..AS: S:: R.KSSL::S R: ......A.K:G :::S:S::L:Q E::EL:R

      Human: ARRLAKSLAILLGVFAVCWAPYSLFTIVLSFYSSATGPKSVWYRIAFWLQWFNSFVNPLLYPLCHKRFQKAFLKIFCIKKQPLPSQHSRSVSS 390
 Guinea Pig: ARKLAKSLAILLAAFAICWAPYSLTTVIYSFFPERNLTKSTWYHTAFWLQWFNSFVNPFLYPLCHKRFQKAFLKILPVRRQSTPP-HNRSIST 389
      Mouse: GRKLARSLAILLSAFAICWAPYCLFTIVLSTYPRTERPKSVWYSIAFWLQWFNSFVNPFLYPLCHRRFQKAFWKILCVTKQPALSQ-NQSVSS 391
        Rat: GRKLARSLAVLLSAFAICWAPYCLFTIVLSTYRRGERPKSIWYSIAFWLQWFNSLINPFLYPLCHRRFQKAFWKILCVTKQPAPSQ-TQSVSS 391
  Consensus: .R:LA:SLA:LL:.FA:CWAPY:L T:: S ::. . .KS.WY:.AFWLQWFNS::NP:LYPLCH:RFQKAF.KI: :::Q: .:  :RS:S:
                         TM6                          TM7
```

DNAS ENCODING GUINEA PIG HISTAMINE RECEPTORS OF THE H4 SUBTYPE

CROSS-REFERENCE TO RELATED APPLICATIONS

This is a divisional of U.S. patent application Ser. No. 09/790,849, filed Feb. 22, 2001, now abandoned, which claims benefit of U.S. Provisional Application Ser. No. 60/208,260, filed May 31, 2000, now expired, the contents of both applications being incorporated in their entireties herein by reference.

BACKGROUND OF THE INVENTION

Histamine is a multifunctional chemical transmitter that signals through cell surface receptors that are linked to intracellular pathways via guanine nucleotide binding proteins. This class of cell surface receptor is called G-protein coupled receptors or GPCRs. There are currently three subtypes of histamine receptors that have been defined pharmacologically and have been divided into H1, H2, and H3 classifications (Hill, et al. 1997). The H1 histamine receptor has been cloned (Yamashita, et al. 1991) and is the target of drugs such as diphenhydramine to block the effects of histamine on smooth muscle in allergic responses. The H2 histamine receptor has been cloned (Gantz et al. 1991) and is the target of drugs such as ranitidine to block the effects of histamine on acid secretion in the stomach. The H3 histamine receptor, which was hypothesized to exist in 1983 (Arrang, et al. 1983), has been cloned (Lovenberg et al., 1999) and is currently a target for development of central nervous system drugs. There are numerous additional functions of histamine in humans which may be mediated by histamine receptors of unknown class. For example, histamine is a chemotactic factor for leukocytes, causing their accumulation in areas of allergic challenge such as skin, nose, eyes and lungs (De Vos, 1999). The receptor responsible for mediating this effect of histamine is not known.

The present invention relates to the isolation and characterization of mammalian cDNAs encoding a novel histamine receptor (histamine H4 receptor) and the uses thereof.

SUMMARY OF THE INVENTION

DNA molecules encoding a mammalian histamine H4 receptor have been cloned and characterized and represent a novel member of the class of receptors that couple to G-proteins. Using a recombinant expression system, functional DNA molecules encoding these histamine H4 receptors have been isolated from mouse, rat, guinea pig, and human. The biological and structural properties of these proteins are disclosed, as is the amino acid and nucleotide sequence. The recombinant protein is useful for a variety of purposes, including but not limited to identifying modulators of the human histamine H4 receptor. The histamine H4 receptors of mouse, rat, and guinea pig have a variety of uses, including but not limited to resolving pharmacological differences observed between different mammalian species, particularly since guinea pig, rat, and murine species are commonly used in pre-clinical evaluation of new chemical entities. Such modulators can include agonists, antagonists, and inverse agonists. Modulators identified in the assays disclosed herein are useful, for example, as therapeutic agents, prophylactic agents, and diagnostic agents. Indications for said therapeutic agents include, but are not limited to, asthma, allergy, inflammation, cardiovascular and cerebrovascular disorders, non-insulin dependent diabetes mellitus, hyperglycemia, constipation, arrhythmia, disorders of the neuroendocrine system, stress, and spasticity, as well as acid secretin, ulcers, airway constriction, and prostate dysfunction. The recombinant DNA molecules, and portions thereof, have a variety of uses including but not limited to isolating homologues of the DNA molecules, identifying and isolating genomic equivalents of the DNA molecules, and identifying, detecting or isolating mutant forms of the DNA molecules.

BRIEF DESCRIPTION OF THE DRAWINGS

FIG. 1—The complete nucleotide coding sequence of human histamine H4 receptor (SEQ ID NO: 1) including untranslated regions is shown.

FIG. 2—The amino acid sequence of human histamine H4 receptor (SEQ ID NO: 2) is shown.

FIG. 3—The tissue distribution of the human histamine H4 receptor is shown.

FIG. 4—Binding of [$^3$H]-histamine to the human H4 receptor is shown.

FIG. 5 Panels A, B and C—The complete nucleotide coding sequence of mouse (A), guinea pig (B), and rat (C) histamine H4 receptors is shown.

FIG. 6 Panels A, B and C—The amino acid sequence of mouse (A) (SEQ ID NO: 5), guinea pig (B) (SEQ ID NO: 7), and rat (C) (SEQ ID NO: 6) histamine H4 receptors is shown.

FIG. 7—The alignment of the polynucleotide sequences of the human, guinea pig, mouse and rat histamine H4 receptor is shown.

FIG. 8—The alignment of the polypeptide sequences of the human, guinea pig (SEQ ID NO: 10), mouse (SEQ ID NO: 8) and rat (SEQ ID NO: 9) histamine H4 receptor is shown.

DETAILED DESCRIPTION

The present invention relates to DNA encoding human histamine H4 receptors that was isolated from a cDNA library from human bone marrow. The human histamine H4 receptor, as used herein, refers to protein which can specifically function as a receptor for histamine of the H4 subclass.

The present invention also relates to DNA molecules encoding mammalian histamine H4 receptors. In particular, the present invention relates to DNA molecules encoding guinea pig (*cavia porcellus*), rat (*rattus rattus*), and murine (*mus musculus*) histamine H4 receptors. The term mammalian histamine H4 receptor, as used herein, refers to protein which can specifically function as a receptor for histamine of the H4 subclass.

The complete or partial amino acid sequence of human, guinea pig, rat, or murine histamine H4 receptor was not previously known, nor was the complete or partial nucleotide sequence encoding histamine H4 receptor known. It is predicted that a wide variety of cells and cell types will contain the described mammalian histamine H4 receptor. Vertebrate cells capable of producing histamine H4 receptor include, but are not limited to histamine H4 receptor expressing cells isolated from cells that show sensitivity to or bind histamine. Such cells can be derived from bone marrow, spleen, blood, or other tissues.

Other cells and cell lines may also be suitable for use to isolate histamine H4 receptor cDNA. Selection of suitable cells may be done by screening for $^3$[H]-histamine binding or inhibition of adenylate cyclase in response to histamine.

Histamine H4 receptor activity can be monitored by performing a $^{3}$[H]-histamine binding assay (see experimental section) or by direct measurement of inhibition of adenylate cyclase due to histamine H4 receptor activation or by incorporation of GTP-gamma-S (Clark, Korte et al. 1993). Cells that possess histamine H4 receptor activity in this assay may be suitable for the isolation of histamine H4 receptor DNA or mRNA.

Any of a variety of procedures known in the art may be used to clone mammalian histamine H4 receptor DNA. These methods include, but are not limited to, direct functional expression of the histamine H4 receptor genes following the construction of a histamine H4 receptor-containing cDNA library in an appropriate expression vector system. Another method is to screen histamine H4 receptor-containing cDNA library constructed in a bacteriophage or plasmid shuttle vector with a labelled oligonucleotide probe designed from the amino acid sequence of the human histamine H4 receptor. An additional method consists of screening a histamine H4 receptor-containing cDNA library constructed in a bacteriophage or plasmid shuttle vector with a partial cDNA encoding the histamine H4 receptor protein. This partial cDNA is obtained by the specific PCR amplification of human histamine H4 receptor DNA fragments through the design of degenerate oligonucleotide primers from the amino acid sequence of the purified histamine H4 receptor protein, described herein.

Another method is to isolate RNA from histamine H4 receptor-producing cells and translate the RNA into protein via an in vitro or an in vivo translation system. The translation of the RNA into a peptide or a protein will result in the production of at least a portion of the histamine H4 receptor protein that can be identified by, for example, immunological reactivity with an anti-histamine H4 receptor antibody or by biological activity of histamine H4 receptor protein. In this method, pools of RNA isolated from histamine H4 receptor-producing cells can be analyzed for the presence of an RNA which encodes at least a portion of the histamine H4 receptor protein. Further fractionation of the RNA pool can be done to purify the histamine H4 receptor RNA from non-histamine H4 receptor RNA. The peptide or protein produced by this method may be analyzed to provide amino acid sequences which in turn are used to provide primers for production of histamine H4 receptor cDNA, or the RNA used for translation can be analyzed to provide nucleotide sequences encoding histamine H4 receptor and produce probes for this production of histamine H4 receptor cDNA. This method is known in the art and can be found in, for example, Maniatis, T., Fritsch, E. F., Sambrook, J. in Molecular Cloning: A Laboratory Manual, Second Edition, Cold Spring Harbor Laboratory Press, Cold Spring Harbor, N.Y. 1989.

It is readily apparent to those skilled in the art that other types of libraries, as well as libraries constructed from other cells or cell types, may be useful for isolating histamine H4 receptor-encoding DNA. Other types of libraries include, but are not limited to, cDNA libraries derived from other cells, from organisms other than human, and genomic DNA libraries that include YAC (yeast artificial chromosome) and cosmid libraries.

It is readily apparent to those skilled in the art that suitable cDNA libraries may be prepared from cells or cell lines which have histamine H4 receptor activity. The selection of cells or cell lines for use in preparing a cDNA library to isolate histamine H4 receptor cDNA may be done by first measuring cell associated histamine H4 receptor activity using the measurement of histamine H4 receptor-associated biological activity or a $^{3}$H-histamine binding assay or any radioligand binding involving a ligand that has the ability to bind to the histamine H4 receptor.

Preparation of cDNA libraries can be performed by standard techniques well known in the art. Well known cDNA library construction techniques can be found for example, in Maniatis, T., Fritsch, E. F., Sambrook, J., Molecular Cloning: A Laboratory Manual, Second Edition (Cold Spring Harbor Laboratory, Cold Spring Harbor, N.Y., 1989).

It is also readily apparent to those skilled in the art that DNA encoding histamine H4 receptor may also be isolated from a suitable genomic DNA library. Construction of genomic DNA libraries can be performed by standard techniques well known in the art. Well known genomic DNA library construction techniques can be found in Maniatis, T., Fritsch, E. F., Sambrook, J. in Molecular Cloning: A Laboratory Manual, Second Edition (Cold Spring Harbor Laboratory, Cold Spring Harbor, N.Y., 1989).

Other mammalian histamine H4 receptor cDNAs may be isolated by conducting PCR or RACE using identical or degenerate primers designed based on the sequences of guinea pig, rat, murine, or human histamine H4 receptor. PCR products are isolated and the sequence is determined and compared to the histamine H4 receptor sequences described herein to establish the identity of other mammalian histamine H4 receptor cDNAs.

In order to clone the histamine H4 receptor gene by the above methods, the amino acid sequence of histamine H4 receptor may be necessary. To accomplish this, histamine H4 receptor protein may be purified and partial amino acid sequence determined by automated sequencers. The predicted amino acid sequence of human, guinea pig, rat, and murine histamine H4 receptors is described herein, and may also be used to assist in cloning the histamine H4 gene. It is not necessary to determine the entire amino acid sequence, but the linear sequence of two regions of about 6 to 8 amino acids from the protein is determined for the production of primers for PCR amplification of a partial human histamine H4 receptor DNA fragment.

Once suitable amino acid sequences have been identified, the DNA sequences capable of encoding them are synthesized. Because the genetic code is degenerate, more than one codon may be used to encode a particular amino acid, and therefore, the amino acid sequence can be encoded by any of a set of similar DNA oligonucleotides. Only one member of the set will be identical to the histamine H4 receptor sequence but will be capable of hybridizing to histamine H4 receptor DNA even in the presence of DNA oligonucleotides with mismatches. The mismatched DNA oligonucleotides may still sufficiently hybridize to the histamine H4 receptor DNA to permit identification and isolation of histamine H4 receptor encoding DNA. DNA isolated by these methods can be used to screen DNA libraries from a variety of cell types, from invertebrate and vertebrate sources, and to isolate homologous genes.

Purified biologically active histamine H4 receptor may have several different physical forms. Histamine H4 receptor may exist as a full-length nascent or unprocessed polypeptide, or as partially processed polypeptides or combinations of processed polypeptides. The full-length nascent histamine H4 receptor polypeptide may be post-translationally modified by specific proteolytic cleavage events which result in the formation of fragments of the full length nascent polypeptide. One example of this is the cleavage of the signal peptide after translation into the endoplasmic reticulum. A fragment, or physical association of fragments may have the full biological activity associated with histamine H4 receptor however, the degree of histamine H4 receptor activity may vary between individual histamine H4 receptor fragments and physically associated histamine H4 receptor polypeptide fragments.

The cloned histamine H4 receptor DNA obtained through the methods described herein may be recombinantly expressed by molecular cloning into an expression vector containing a suitable promoter and other appropriate transcription regulatory elements, and transferred into prokaryotic or eukaryotic host cells to produce recombinant histamine H4 receptor protein. Techniques for such manipulations are fully described in Maniatis, T, et al., supra, and are well known in the art.

Expression vectors are defined herein as DNA sequences that are required for the transcription of cloned copies of genes and the translation of their mRNAs in an appropriate host. Such vectors can be used to express eukaryotic genes in a variety of hosts such as bacteria including *E. coli*, blue-green algae, plant cells, insect cells, fungal cells including yeast cells, and animal cells.

Specifically designed vectors allow the shuttling of DNA between hosts such as bacteria-yeast or bacteria-animal cells or bacteria-fungal cells or bacteria-invertebrate cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one that causes mRNAs to be initiated at high frequency and optimally does not greatly limit the proliferation of the host. Expression vectors may include, but are not limited to, cloning vectors, modified cloning vectors, specifically designed plasmids or viruses.

A variety of mammalian expression vectors may be used to express recombinant human histamine H4 receptor in mammalian cells. Commercially available mammalian expression vectors which may be suitable for recombinant mammalian histamine H4 receptor expression, include but are not limited to, pMAMneo (Clontech), pcDNA3 (Invitrogen), pMC1neo (Stratagene), pXT1 (Stratagene), pSG5 (Stratagene), pCIneo (Promega), EBO-pSV2-neo (ATCC 37593) pBPV-1(8-2) (ATCC 37110), pdBPV-MMneo(342-12) (ATCC 37224), pRSVgpt (ATCC 37199), pRSVneo (ATCC 37198), pSV2-dhfr (ATCC 37146), pUCTag (ATCC 37460), and IZD35 (ATCC 37565).

A variety of bacterial expression vectors may be used to express recombinant mammalian histamine H4 receptor in bacterial cells. Commercially available bacterial expression vectors which may be suitable for recombinant mammalian histamine H4 receptor expression include, but are not limited to pET vectors (Novagen) and pQE vectors (Qiagen).

A variety of fungal cell expression vectors may be used to express recombinant mammalian histamine H4 receptor in fungal cells such as yeast. Commercially available fungal cell expression vectors which may be suitable for recombinant mammalian histamine H4 receptor expression include but are not limited to pYES2 (Invitrogen) and *Pichia* expression vector (Invitrogen).

A variety of insect cell expression vectors may be used to express recombinant mammalian histamine H4 receptor in insect cells. Commercially available insect cell expression vectors which may be suitable for recombinant expression of mammalian histamine H4 receptor include but are not limited to pBlueBacII (Invitrogen).

DNA encoding mammalian histamine H4 receptor may be cloned into an expression vector for expression in a recombinant host cell. Recombinant host cells may be prokaryotic or eukaryotic, including but not limited to bacteria such as *E. coli*, fungal cells such as yeast, mammalian cells including but not limited to cell lines of human, bovine, porcine, monkey and rodent origin, and insect cells including but not limited to *drosophila* and silkworm derived cells. Cell lines derived from mammalian species which may be suitable and which are commercially available, include but are not limited to, CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26), MRC-5 (ATCC CCL 171), L-cells, and HEK-293 (ATCC CRL1573).

The expression vector may be introduced into host cells via any one of a number of techniques including but not limited to transformation, transfection, protoplast fusion, lipofection, and electroporation. The expression vector-containing cells are clonally propagated and individually analyzed to determine whether they produce mammalian histamine H4 receptor protein. Identification of mammalian histamine H4 receptor expressing host cell clones may be done by several means, including but not limited to immunological reactivity with anti-mammalian histamine H4 receptor antibodies, and the presence of host cell-associated mammalian histamine H4 receptor activity.

Expression of mammalian histamine H4 receptor DNA may also be performed using in vitro produced synthetic mRNA. Synthetic mRNA or mRNA isolated from mammalian histamine H4 receptor producing cells can be efficiently translated in various cell-free systems, including but not limited to wheat germ extracts and reticulocyte extracts, as well as efficiently translated in cell based systems, including but not limited to microinjection into frog oocytes, with microinjection into frog oocytes being generally preferred.

To determine the mammalian histamine H4 receptor DNA sequence(s) that yields optimal levels of mammalian histamine H4 receptor activity and/or mammalian histamine H4 receptor protein, human histamine H4 receptor DNA molecules including, but not limited to, the following can be constructed: the full-length open reading frame of the human histamine H4 receptor cDNA encoding the 44,495 Daltons protein from approximately base 1 to base 1173 (these numbers correspond to first nucleotide of first methionine and last nucleotide before the first stop codon) and several constructs containing portions of the cDNA encoding human histamine H4 receptor protein. All constructs can be designed to contain none, all or portions of the 5' or the 3' untranslated region of human histamine H4 receptor cDNA. Human histamine H4 receptor activity and levels of protein expression can be determined following the introduction, both singly and in combination, of these constructs into appropriate host cells. Following determination of the mammalian histamine H4 receptor DNA cassette yielding optimal expression in transient assays, the mammalian histamine H4 receptor DNA construct is transferred to a variety of expression vectors, for expression in host cells including, but not limited to, mammalian cells, baculovirus-infected insect cells, *E. coli*, and the yeast *S. cerevisiae.*

Host cell transfectants and microinjected oocytes may be used to assay both the levels of mammalian histamine H4 receptor activity and levels of mammalian histamine H4 receptor protein by the following methods. In the case of recombinant host cells, this involves the co-transfection of one or possibly two or more plasmids, containing the mammalian histamine H4 receptor DNA encoding one or more fragments or subunits. In the case of oocytes, this involves the co-injection of RNAs encoding mammalian histamine H4 receptor protein. Following an appropriate period of time to allow for expression, cellular protein is metabolically labelled with, for example $^{35}$S-methionine for 24 hours, after which cell lysates and cell culture supernatants are harvested and subjected to immunoprecipitation with polyclonal antibodies directed against the mammalian histamine H4 receptor protein.

Other methods for detecting mammalian histamine H4 receptor activity involve the direct measurement of mammalian histamine H4 receptor activity in whole cells transfected with mammalian histamine H4 receptor cDNA or oocytes injected with mammalian histamine H4 receptor mRNA. Mammalian histamine H4 receptor activity is measured by specific ligand binding, for example [$H^3$]-Histamine, and biological characteristics of the host cells expressing mammalian histamine H4 receptor DNA. In the case of recombinant host cells and oocytes expressing mammalian histamine H4 receptor cAMP quantitation and receptor binding techniques are suitable examples of methods that can be used to measure mammalian histamine H4 receptor activity and quantify mammalian histamine H4 receptor protein.

Levels of mammalian histamine H4 receptor protein in host cells are also quantitated by immunoaffinity and/or ligand affinity techniques. Cells expressing mammalian histamine H4 receptor can be assayed for the number of mammalian histamine H4 receptor molecules expressed by measuring the amount of radioactive histamine or histamine H4 ligand binding to cell membranes. Mammalian histamine H4 receptor-specific affinity beads or mammalian histamine H4 receptor-specific antibodies are used to isolate for example $^{35}$S-methionine labelled or unlabelled mammalian histamine H4 receptor protein. Labelled mammalian histamine H4 receptor protein is analyzed by SDS-PAGE. Unlabelled mammalian histamine H4 receptor protein is detected by Western blotting, ELISA or RIA assays employing mammalian histamine H4 receptor specific antibodies.

Because the genetic code is degenerate, more than one codon may be used to encode a particular amino acid, and therefore, the amino acid sequence can be encoded by any of a set of similar DNA oligonucleotides. Only one member of the set will be identical to the mammalian histamine H4 receptor sequence but will be capable of hybridizing to mammalian histamine H4 receptor DNA even in the presence of DNA oligonucleotides with mismatches under appropriate conditions. Under alternate conditions, the mismatched DNA oligonucleotides may still hybridize to the mammalian histamine H4 receptor DNA to permit identification and isolation of mammalian histamine H4 receptor encoding DNA. Because different species have different codon usage preference, it is preferable to prepare silent mutants of the mammalian Histamine H4 receptor that contain optimized codon usage for the particular expression host.

DNA encoding mammalian histamine H4 receptor from a particular organism may be used to isolate and purify homologues of mammalian histamine H4 receptor from other organisms. To accomplish this, the first mammalian histamine H4 receptor DNA may be mixed with a sample containing DNA encoding homologues of mammalian histamine H4 receptor under appropriate hybridization conditions. The hybridized DNA complex may be isolated and the DNA encoding the homologous DNA may be purified therefrom.

It is known that there is a substantial amount of redundancy in the various codons that code for specific amino acids. Therefore, this invention is also directed to those DNA sequences that contain alternative codons that code for the eventual translation of the identical amino acid. For purposes of this specification, a sequence bearing one or more replaced codons will be defined as a degenerate variation. Also included within the scope of this invention are mutations either in the DNA sequence or the translated protein that does not substantially alter the ultimate physical properties of the expressed protein. For example, substitution of aliphatic amino acids alanine, valine, leucine and isoleucine, interchange of the hydroxyl residues serine and threonine, exchange of the acidic residues aspartic acid and glutamic acid, substitution between the amide residues asparagine and glutamine, exchange of the basic residues lysine and arginine and substitution among the aromatic residues phenylalanine, tyrosine may not cause a change in functionality of the polypeptide. Another example of a mutation that does not alter the functional properties of the receptor is construction of a chimeric gene expressing a different signal peptide that targets the receptor for translation within the endoplasmic reticulum. Such substitutions are well known and are described, for instance in *Molecular Biology of the Gene,* 4$^{th}$ Ed. Bengamin Cummings Pub. Co. by Watson et al.

It is known that DNA sequences coding for a peptide may be altered so as to code for a peptide having properties that are different than those of the naturally-occurring peptide. Methods of altering the DNA sequences include, but are not limited to site directed mutagenesis or domain swapping (chimeric analysis). Chimeric genes are prepared by swapping domains of similar or different genes to replace similar domains in the mammalian histamine H4 receptor gene. Similarly, fusion genes may be prepared that add domains to the mammalian histamine H4 receptor gene, such as an affinity tag to facilitate identification and isolation of the gene. Fusion genes may be prepared to replace regions of the mammalian histamine H4 receptor gene, for example to add a targeting sequence to redirect the normal transport of the protein or adding new post-translational modification sequences to the mammalian histamine H4 receptor gene (eg. a neoglycosylation site). Examples of altered properties include but are not limited to changes in the affinity of an enzyme for a substrate or a receptor for a ligand. All such changes of the polynucleotide or polypeptide sequences are anticipated as useful variants of the present invention so long as the original function of the polynucleotide or polypeptide sequence of the present invention is maintained as described herein.

Identity or similarity, as known in the art, is relationships between two or more polypeptide sequences or two or more polynucleotide sequences, as determined by comparing the sequences. In the art, identity also means the degree of sequence relatedness between polypeptide or polynucleotide sequences, as the case may be, as determined by the match between strings of such sequences. Both identity and similarity can be readily calculated (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). While there exists a number of methods to measure identity and similarity between two polynucleotide or two polypeptide sequences, both terms are well known to skilled artisans (Sequence Analysis in Molecular Biology, von Heinje, G., Academic Press, 1987; Sequence Analysis Primer, Gribskov, M. and Devereux, J., eds., M Stockton Press, New York, 1991; and Carillo, H., and lipman, D., (1988) SIAM J. Applied Math., 48, 1073. Methods commonly employed to determine identity or similarity between sequences include, but are not limited to those disclosed in Carillo, H., and Lipman, D., (1988) SIAM J. Applied Math., 48, 1073. Preferred methods to determine identity are designed to give the largest match between the sequences tested. Methods to determine identity and similarity are codified in computer programs. Preferred computer program methods to determine identity and similarity between two sequences include, but are not limited to, GCG program package (Devereux, J., et al., (1984) Nucleic Acids Research 12(1), 387), BLASTP, BLASTN, and FASTA (Atschul, S. F. et al., (1990) J. Molec. Biol. 215, 403).

Polynucleotide(s) generally refers to any polyribonucleotide or polydeoxyribonucleotide, which may be unmodified RNA or DNA or modified RNA or DNA. Thus, for instance, polynucleotides as used herein refers to, among others, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded, or a mixture of single- and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term polynucleotide includes DNAs or RNAs as described above that contain one or more modified bases. Thus, DNAs or RNAs with backbones modified for stability or for other reasons are “polynucleotides” as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia. Polynucleotides embraces short polynucleotides often referred to as oligonucleotide(s).

The term polypeptides, as used herein, refers to the basic chemical structure of polypeptides that is well known and has been described in textbooks and other publications in the art. In this context, the term is used herein to refer to any peptide or protein comprising two or more amino acids joined to each other in a linear chain by peptide bonds. As used herein, the term refers to both short chains, which also commonly are referred to in the art as peptides, oligopeptides and oligomers, for example, and to longer chains, which generally are referred to in the art as proteins, of which there are many types. It will be appreciated that polypeptides often contain amino acids other than the 20 amino acids commonly referred to as the 20 naturally occurring amino acids, and that many amino acids, including the terminal amino acids, may be modified in a given polypeptide, either by natural processes, such as processing and other post-translational modifications, but also by chemical modification techniques which are well known to the art. Even the common modifications that occur naturally in polypeptides are too numerous to list exhaustively here, but they are well described in basic texts and in more detailed monographs, as well as in a voluminous research literature, and they are well known to those of skill in the art. Among the known modifications which may be present in polypeptides of the present are, to name an illustrative few, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Such modifications are well known to those of skill and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as, for instance PROTEINS—STRUCTURE AND MOLECULAR PROPERTIES, 2nd Ed., T. E. Creighton, W. H. Freeman and Company, New York (1993). Many detailed reviews are available on this subject, such as, for example, those provided by Wold, F., Post-translational Protein Modifications: Perspectives and Prospects, pgs. 1–12 in POST-TRANSLATIONAL COVALENT MODIFICATION OF PROTEINS, B. C. Johnson, Ed., Academic Press, New York (1983); Seifter et al., (1990) Meth. Enzymol. 182, 626–646 and Rattan et al., “Protein Synthesis: Posttranslational Modifications and Aging”, (1992) Ann. N.Y. Acad. Sci. 663, 48–62. It will be appreciated, as is well known and as noted above, that polypeptides are not always entirely linear. For instance, polypeptides may be generally as a result of posttranslational events, including natural processing event and events brought about by human manipulation which do not occur naturally. Circular, branched and branched circular polypeptides may be synthesized by non-translation natural process and by entirely synthetic methods, as well. Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in *E. coli* or other cells, prior to proteolytic processing, almost invariably will be N-formylmethionine. During post-translational modification of the peptide, a methionine residue at the amino terminus may be deleted. Accordingly, this invention contemplates the use of both the methionine-containing and the methionine-less amino terminal variants of the protein of the invention. The modifications that occur in a polypeptide often will be a function of how it is made. For polypeptides made by expressing a cloned gene in a host, for instance, the nature and extent of the modifications in large part will be determined by the host cell posttranslational modification capacity and the modification signals present in the polypeptide amino acid sequence. For instance, as is well known, glycosylation often does not occur in bacterial hosts such as, for example, *E. coli*. Accordingly, when glycosylation is desired, a polypeptide should be expressed in a glycosylating host, generally a eukaryotic cell. Insect cell often carry out the same posttranslational glycosylations as mammalian cells and, for this reason, insect cell expression systems have been developed to express efficiently mammalian proteins having native patterns of glycosylation, inter alia. Similar considerations apply to other modifications. It will be appreciated that the same type of modification may be present in the same or varying degree at several sites in a given polypeptide. Also, a given polypeptide may contain many types of modifications. In general, as used herein, the term polypeptide encompasses all such modifications, particularly those that are present in polypeptides synthesized recombinantly by expressing a polynucleotide in a host cell.

Variant(s) of polynucleotides or polypeptides, as the term is used herein, are polynucleotides or polypeptides that differ from a reference polynucleotide or polypeptide, respectively. A variant of the polynucleotide may be a naturally occurring variant such as a naturally occurring allelic variant, or it may be a variant that is not known to occur naturally. (1) A polynucleotide that differs in nucleotide sequence from another, reference polynucleotide. Generally, differences are limited so that the nucleotide sequences of the reference and the variant are closely similar overall and, in many regions, identical. As noted below, changes in the nucleotide sequence of the variant may be silent. That is, they may not alter the amino acids encoded by the polynucleotide. Where alterations are limited to silent changes of this type a variant will encode a polypeptide with the same amino acid sequence as the reference. Also as noted below, changes in the nucleotide sequence of the variant may alter the amino acid sequence of a polypeptide encoded by the reference polynucleotide. Such nucleotide changes may result in amino acid substitutions, additions, deletions, fusions and truncations in the polypeptide encoded by the reference sequence, as discussed above. (2) A polypeptide that differs in amino acid sequence from another, reference polypeptide. Generally, differences are limited so that the sequences of the reference and the variant are closely similar overall and, in many regions, identical. A variant and reference polypeptide may differ in amino acid sequence by one or more substitutions, additions, deletions, fusions and truncations, which may be present in any combination. As used herein, a "functional derivative" of histamine H4 receptor is a compound that possesses a biological activity (either functional or structural) that is substantially similar to the biological activity of histamine H4 receptor. The term "functional derivatives" is intended to include the "fragments," "variants," "degenerate variants," "analogs" and "homologues" or to "chemical derivatives" of histamine H4 receptor. Useful chemical derivatives of polypeptide are well known in the art and include, for example covalent modification of reactive organic site contained within the polypeptide with a secondary chemical moiety. Well known cross-linking reagents are useful to react to amino, carboxyl, or aldehyde residues to introduce, for example an affinity tag such as biotin, a fluorescent dye, or to conjugate the polypeptide to a solid phase surface (for example to create an affinity resin). The term "fragment" is meant to refer to any polypeptide subset of histamine H4 receptor. A molecule is "substantially similar" to histamine H4 receptor if both molecules have substantially similar structures or if both molecules possess similar biological activity. Therefore, if the two molecules possess substantially similar activity, they are considered to be variants even if the structure of one of the molecules is not found in the other or even if the two amino acid sequences are not identical. The term "analog" refers to a molecule substantially similar in function to either the entire histamine H4 receptor molecule or to a fragment thereof. Further particularly preferred in this regard are polynucleotides encoding variants, analogs, derivatives and fragments of any one of SEQ. ID. NO.:1, 5, 6, or 7, and variants, analogs and derivatives of the fragments, which have the amino acid sequence corresponding to the polypeptide set forth in SEQ. ID. NO.:2, 8, 9, 10 respectively in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the gene of any one of SEQ. ID. NO.:1, 5, 6, or 7. Also especially preferred in this regard are conservative substitutions. Most highly preferred are polynucleotides encoding polypeptides having the amino acid sequence of any one of SEQ. ID. NO.:2, 8, 9, and 10, without substitutions.

Further preferred embodiments of the invention are polynucleotides that are at least 70% identical over their entire length to a polynucleotide encoding the polypeptide having the amino acid sequence set out in any one of SEQ. ID. NO.:2, 8, 9, 10, and polynucleotides which are complementary to such polynucleotides. Alternatively, highly preferred are polynucleotides that comprise a region that is at least 80% identical, more highly preferred are polynucleotides at comprise a region that is at least 90% identical, and among these preferred polynucleotides, those with at least 95% are especially preferred. Furthermore, those with at least 97% identity are highly preferred among those with at least 95%, and among these those with at least 98% and at least 99% are particularly highly preferred, with at least 99% being the most preferred. The polynucleotides which hybridize to the polynucleotides of the present invention, in a preferred embodiment encode polypeptides which retain substantially the same biological function or activity as the polypeptide characterized by the deduced amino acid sequence of any one of SEQ. ID. NO.:2, 8, 9, or 10. Preferred embodiments in this respect, moreover, are polynucleotides that encode polypeptides that retain substantially the same biological function or activity as the mature polypeptide encoded by the DNA of any one of SEQ. ID. NO.:1, 5, 6, or 7. The present invention further relates to polynucleotides that hybridize to the herein above-described sequences. In this regard, the present invention especially relates to polynucleotides that hybridize under stringent conditions to the herein above-described polynucleotides. As herein used, the term "stringent conditions" means hybridization will occur only if there is at least 95% and preferably at least 97% identity between the sequences.

Polynucleotides of the present invention may be used as a hybridization probe for RNA, cDNA and genomic DNA to isolate full-length cDNAs and genomic clones encoding the sequences of any one of SEQ. ID. NO.:1, 5, 6, or 7 and to isolate cDNA and genomic clones of other genes that have a high sequence similarity to any one of SEQ. ID. NO.:1, 5, 6, or 7. Such probes generally will comprise at least 15 bases. Preferably, such probes will have at least 30 bases and may have at least 50 bases. Particularly preferred probes will have at least 30 bases and will have 50 bases or less. For example, the coding region of the gene of the invention may be isolated by screening using the known DNA sequence to synthesize an oligonucleotide probe. A labeled oligonucleotide having a sequence complementary to that of a gene of the present invention is then used to screen a library of cDNA, genomic DNA or mRNA to determine to which members of the library the probe hybridizes.

The polypeptides of the present invention include the polypeptide of any one of SEQ. ID. NO.:2, 8, 9, 10 (in particular the mature polypeptide) as well as polypeptides which have at least 70% identity to the polypeptide of any one of SEQ. ID. NO.:2, 8, 9, 10, preferably at least 80% identity to the polypeptide of any one of SEQ. ID. NO.:2, 8, 9, 10, and more preferably at least 90% similarity (more preferably at least 90% identity) to the polypeptide of any one of SEQ. ID. NO.:2, 8, 9, 10 and still more preferably at least 95% similarity (still more preferably at least 97% identity) to the polypeptide of any one of SEQ. ID. NO.:2, 8, 9, 10 and also include portions of such polypeptides with such portion of the polypeptide generally containing at least 30 amino acids and more preferably at least 50 amino acids. Representative examples of polypeptide fragments of the invention, include, for example, truncation polypeptides of any one of SEQ. ID. NO.:2, 8, 9, 10. Truncation polypeptides include polypeptides having the amino acid sequence of any one of SEQ. ID. NO.:2, 8, 9, 10, or of variants or derivatives thereof, except for deletion of a continuous series of residues (that is, a continuous region, part or portion) that includes the amino terminus, or a continuous series of residues that includes the carboxyl terminus or, as in double truncation mutants, deletion of two continuous series of residues, one including the amino terminus and one including the carboxyl terminus. Also preferred in this aspect of the invention are fragments characterized by structural or functional attributes of the polypeptide characterized by the sequences of any one of SEQ. ID. NO.:2, 8, 9, 10. Preferred embodiments of the invention in this regard include fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, high antigenic index regions of the polypeptide of the invention, and combinations of such fragments. Preferred regions are those that mediate activities of the polypeptides of the invention. Most highly preferred in this regard are fragments that have a chemical, biological or other activity of the response regulator polypeptide of the invention, including those with a similar activity or an improved activity, or with a decreased undesirable activity.

Monospecific antibodies to mammalian histamine H4 receptor are purified from mammalian antisera containing antibodies reactive against mammalian histamine H4 receptor or are prepared as monoclonal antibodies reactive with mammalian histamine H4 receptor using the technique of Kohler and Milstein, *Nature* 256: 495–497 (1975). Monospecific antibody as used herein is defined as a single antibody species or multiple antibody species with homogenous binding characteristics for mammalian histamine H4 receptor. Homogenous binding as used herein refers to the ability of the antibody species to bind to a specific antigen or epitope, such as those associated with the mammalian histamine H4 receptor, as described above. Mammalian histamine H4 receptor specific antibodies are raised by immunizing animals such as mice, rats, guinea pigs, rabbits, goats, horses and the like, with rabbits being preferred, with an appropriate concentration of mammalian histamine H4 receptor either with or without an immune adjuvant.

Preimmune serum is collected prior to the first immunization. Each animal receives between about 0.1 mg and about 1000 mg of mammalian histamine H4 receptor associated with an acceptable immune adjuvant. Such acceptable adjuvants include, but are not limited to, Freund's complete, Freund's incomplete, alum-precipitate, water in oil emulsion containing *Corynebacterium parvum* and tRNA. The initial immunization consists of mammalian histamine H4 receptor in, preferably, Freund's complete adjuvant at multiple sites either subcutaneously (SC), intraperitoneally (IP) or both. Each animal is bled at regular intervals, preferably weekly, to determine antibody titer. The animals may or may not receive booster injections following the initial immunization. Those animals receiving booster injections are generally given an equal amount of the antigen in Freund's incomplete adjuvant by the same route. Booster injections are given at about three week intervals until maximal titers are obtained. At about 7 days after each booster immunization or about weekly after a single immunization, the animals are bled, the serum collected, and aliquots are stored at about −20° C.

Monoclonal antibodies (mAb) reactive with mammalian histamine H4 receptor are prepared by immunizing inbred mice, preferably Balb/c, with is mammalian histamine H4 receptor and any fragments thereof. The mice are immunized by the IP or SC route with about 0.1 mg to about 10 mg, preferably about 1 mg, of mammalian histamine H4 receptor in about 0.5 ml buffer or saline incorporated in an equal volume of an acceptable adjuvant, as discussed above. Freund's complete adjuvant is preferred. The mice receive an initial immunization on day 0 and are rested for about 3 to about 30 weeks. Immunized mice are given one or more booster immunizations of about 0.1 to about 10 mg of mammalian histamine H4 receptor in a buffer solution such as phosphate buffered saline by the intravenous (IV) route. Lymphocytes, from antibody positive mice, preferably splenic lymphocytes, are obtained by removing spleens from immunized mice by standard procedures known in the art. Hybridoma cells are produced by mixing the splenic lymphocytes with an appropriate fusion partner, preferably myeloma cells, under conditions which will allow the formation of stable hybridomas. Fusion partners may include, but are not limited to: mouse myelomas P3/NS1/Ag 4-1; MPC-11; S-194 and Sp 2/0, with Sp 2/0 being generally preferred. The antibody producing cells and myeloma cells are fused in polyethylene glycol, about 1000 mol. wt., at concentrations from about 30% to about 50%. Fused hybridoma cells are selected by growth in hypoxanthine, thymidine and aminopterin supplemented Dulbecco's Modified Eagles Medium (DMEM) by procedures known in the art. Supernatant fluids are collected from growth positive wells on about days 14, 18, and 21 and are screened for antibody production by an immunoassay such as solid phase immunoradioassay (SPIRA) using mammalian histamine H4 receptor as the antigen. The culture fluids are also tested in the Ouchterlony precipitation assay to determine the isotype of the mAb. Hybridoma cells from antibody positive wells are cloned by a technique such as the soft agar technique of MacPherson, Soft Agar Techniques, in Tissue Culture Methods and Applications, Kruse and Paterson, Eds., Academic Press, 1973.

Monoclonal antibodies are produced in vivo by injection of pristane primed Balb/c mice, approximately 0.5 ml per mouse, with about $2\times10^6$ to about $6\times10^6$ hybridoma cells about 4 days after priming. Ascites fluid is collected at approximately 8–12 days after cell transfer and the monoclonal antibodies are purified by techniques known in the art.

In vitro production of anti-mammalian histamine H4 receptor mAb is carried out by growing the hybridoma in DMEM containing about 2% fetal calf serum to obtain sufficient quantities of the specific mAb. The mAb are purified by techniques known in the art.

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques. Similar assays are used to detect the presence of mammalian histamine H4 receptor in body fluids or tissue and cell extracts.

It is readily apparent to those skilled in the art that the above described methods for producing monospecific antibodies may be utilized to produce antibodies specific for mammalian histamine H4 receptor polypeptide fragments, or full-length nascent mammalian histamine H4 receptor polypeptide, or the individual mammalian histamine H4 receptor subunits. Specifically, it is readily apparent to those skilled in the art that monospecific antibodies may be generated which are specific for only one mammalian histamine H4 receptor subunit or the fully functional histamine H4 receptor.

DNA clones, termed pH4R, are identified which encode proteins that, when expressed in any recombinant host, including but not limited to mammalian cells or insect cells or bacteria, form a mammalian histamine H4 receptor sensitive to histamine or other histamine H4 ligands. The expression of mammalian histamine H4 receptor DNA results in the expression of the properties observed with mammalian histamine H4 receptor.

Histamine is a biogenic amine transmitter that functions in some capacity in nearly all physiological and pathophysiological situations. Histamine acts as a neurotransmitter and neuromodulator in the central nervous system, mediates inflammatory and allergic responses, regulates airway function, controls acid secretion in the stomach, regulates cardiovascular function as well as arterial and venous responses and is without doubt involved in processes yet to be determined. The histamine receptors that mediate these effects are not completely characterized. One way to understand which histamine receptors are involved in these processes is to develop chemical modulators (agonists, antagonists, and inverse agonists) of the receptors as research tools and therapeutic entities. Recombinant host cells expressing the mammalian histamine H4 receptor can be used to provide materials for a screening method to identify such agonists and antagonists. As such, this invention of the mammalian histamine H4 receptor directly teaches a way to identify new agonists and antagonists that may prove useful as research tools or may be used as therapeutics to treat disorders directly or indirectly involving histamine receptors. Assays to detect compound interaction or modulation of the histamine H4 receptor include, but are not limited to, direct ligand binding assays, competitive (or displacement) ligand binding assays, or functional assays that measure the response of the receptor to the ligand, for example by production of cAMP. Although these assays are well known to those skilled in the art, they were previously no possible prior to obtaining the recombinant molecules taught herein.

The present invention is also directed to methods for screening for compounds that modulate the expression of DNA or RNA encoding mammalian histamine H4 receptor as well as the function of mammalian histamine H4 receptor protein in vivo. Compounds that modulate these activities may be DNA, RNA, peptides, proteins, or non-proteinaceous organic molecules. Compounds may modulate by increasing or attenuating the expression of DNA or RNA encoding mammalian histamine H4 receptor, or the function of mammalian histamine H4 receptor protein. Compounds that modulate the expression of DNA or RNA encoding mammalian histamine H4 receptor or the function of mammalian histamine H4 receptor protein may be detected by a variety of assays. The assay may be a simple "yes/no" assay to determine whether there is a change in expression or function. The assay may be made quantitative by comparing the expression or function of a test sample with the levels of expression or function in a standard sample. Modulators identified in this process are useful as therapeutic agents, research tools, and diagnostic agents.

Kits containing mammalian histamine H4 receptor DNA or RNA, antibodies to mammalian histamine H4 receptor, or mammalian histamine H4 receptor protein may be prepared. Such kits are used to detect DNA that hybridizes to mammalian histamine H4 receptor DNA or to detect the presence of mammalian histamine H4 receptor protein or peptide fragments in a sample. Such characterization is useful for a variety of purposes including but not limited to forensic analyses, diagnostic applications, and epidemiological studies.

The DNA molecules, RNA molecules, recombinant protein and antibodies of the present invention may be used to screen and measure levels of mammalian histamine H4 receptor DNA, mammalian histamine H4 receptor RNA or mammalian histamine H4 receptor protein. The recombinant proteins, DNA molecules, RNA molecules and antibodies lend themselves to the formulation of kits suitable for the detection and typing of mammalian histamine H4 receptor. Such a kit would comprise a compartmentalized carrier suitable; to hold in close confinement at least one container. The carrier would further comprise reagents such as recombinant mammalian histamine H4 receptor protein or anti-mammalian histamine H4 receptor antibodies suitable for detecting mammalian histamine H4 receptor. The carrier may also contain a means for detection such as labeled antigen or enzyme substrates or the like.

Nucleotide sequences that are complementary to the mammalian histamine H4 receptor encoding DNA sequence can be synthesized for antisense therapy. These antisense molecules may be DNA, stable derivatives of DNA such as phosphorothioates or methylphosphonates, RNA, stable derivatives of RNA such as 2'-O-alkylRNA, or other mammalian histamine H4 receptor antisense oligonucleotide mimetics. Mammalian histamine H4 receptor antisense molecules may be introduced into cells by microinjection, liposome encapsulation or by expression from vectors harboring the antisense sequence, mammalian histamine H4 receptor antisense therapy may be particularly useful for the treatment of diseases where it is beneficial to reduce mammalian histamine H4 receptor activity.

Mammalian histamine H4 receptor gene therapy may be used to introduce mammalian histamine H4 receptor into the cells of target organisms. The mammalian histamine H4 receptor gene can be ligated into viral vectors which mediate transfer of the mammalian histamine H4 receptor DNA by infection of recipient host cells. Suitable viral vectors include retrovirus, adenovirus, adeno-associated virus, herpes virus, vaccinia virus, polio virus and the like. Alternatively, mammalian histamine H4 receptor DNA can be transferred into cells for gene therapy by non-viral techniques including receptor-mediated targeted DNA transfer using ligand-DNA conjugates or adenovirus-ligand-DNA conjugates, lipofection membrane fusion or direct microinjection. These procedures and variations thereof are suitable for ex vivo as well as in vivo mammalian histamine H4 receptor gene therapy. Mammalian histamine H4 receptor gene therapy may be particularly useful for the treatment of diseases where it is beneficial to elevate mammalian histamine H4 receptor activity.

Pharmaceutically useful compositions comprising mammalian histamine H4 receptor DNA, mammalian histamine H4 receptor RNA, or mammalian histamine H4 receptor protein, or modulators of mammalian histamine H4 receptor activity, may be formulated according to known methods such as by the admixture of a pharmaceutically acceptable carrier. Examples of such carriers and methods of formulation may be found in Remington's Pharmaceutical Sciences. To form a pharmaceutically acceptable composition suitable for effective administration, such compositions will contain an effective amount of the protein, DNA, RNA, or modulator.

Therapeutic or diagnostic compositions of the invention are administered to an individual in amounts sufficient to treat or diagnose disorders in which modulation of mammalian histamine H4 receptor-related activity is indicated. The effective amount may vary according to a variety of factors such as the individual's condition, weight, sex and age. Other factors include the mode of administration. The pharmaceutical compositions may be provided to the individual by a variety of routes such as subcutaneous, topical, oral and intramuscular.

The term "chemical derivative" describes a molecule that contains additional chemical moieties that are not normally a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as Remington's Pharmaceutical Sciences.

Compounds identified according to the methods disclosed herein may be used alone at appropriate dosages defined by routine testing in order to obtain optimal inhibition of the mammalian histamine H4 receptor or its activity while minimizing any potential toxicity. In addition, co-administration or sequential administration of other agents may be desirable.

The present invention also has the objective of providing suitable topical, oral, systemic and parenteral pharmaceutical formulations for use in the novel methods of treatment of the present invention. The compositions containing compounds or modulators identified according to this invention as the active ingredient for use in the modulation of mammalian histamine H4 receptor receptors can be administered in a wide variety of therapeutic dosage forms in conventional vehicles for administration. For example, the compounds or modulators can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the compound desired can be employed as a mammalian histamine H4 receptor modulating agent.

The daily dosage of the products may be varied over a wide range from 0.01 to 1,000 mg per patient, per day. For oral administration, the compositions are preferably provided in the form of scored or un-scored tablets containing 0.01, 0.05, 0.1, 0.5, 1.0, 2.5, 5.0, 10.0, 15.0, 25.0, and 50.0 milligrams of the active ingredient for the symptomatic adjustment of the dosage to the patient to be treated. An effective amount of the drug is ordinarily supplied at a dosage level of from about 0.0001 mg/kg to about 100 mg/kg of body weight per day. The range is more particularly from about 0.001 mg/kg to 10 mg/kg of body weight per day. The dosages of the mammalian histamine H4 receptor modulators are adjusted when combined to achieve desired effects. On the other hand, dosages of these various agents may be independently optimized and combined to achieve a synergistic result wherein the pathology is reduced more than it would be if either agent were used alone.

Advantageously, compounds or modulators of the present invention may be administered in a single daily dose, or the total daily dosage may be administered in divided doses of two, three or four times daily. Furthermore, compounds or modulators for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

For combination treatment with more than one active agent, where the active agents are in separate dosage formulations, the active agents can be administered concurrently, or they each can be administered at separately staggered times.

The dosage regimen utilizing the compounds or modulators of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug.

In the methods of the present invention, the compounds or modulators herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

For liquid forms the active drug component can be combined in suitably flavored suspending or dispersing agents such as the synthetic and natural gums, for example, tragacanth, acacia, methyl-cellulose and the like. Other dispersing agents which may be employed include glycerin and the like. For parenteral administration, sterile suspensions and solutions are desired. Isotonic preparations which generally contain suitable preservatives are employed when intravenous administration is desired.

Topical preparations containing the active drug component can be admixed with a variety of carrier materials well known in the art, such as, eg., alcohols, aloe vera gel, allantoin, glycerine, vitamin A and E oils, mineral oil, PPG2 myristyl propionate, and the like, to form, eg., alcoholic solutions, topical cleansers, cleansing creams, skin gels, skin lotions, and shampoos in cream or gel formulations.

The compounds or modulators of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds or modulators of the present invention may also be coupled with soluble polymers as targetable drug carriers. Such polymers can include polyvinyl-pyrrolidone, pyran copolymer, polyhydroxypropylmethacryl-amidephenol, polyhydroxy-ethylaspartamidephenol, or polyethyl-eneoxidepolylysine substituted with palmitoyl residues. Furthermore, the compounds or modulators of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

For oral administration, the compounds or modulators may be administered in capsule, tablet, or bolus form or alternatively they can be mixed in the animals feed. The capsules, tablets, and boluses are comprised of the active ingredient in combination with an appropriate carrier vehicle such as starch, talc, magnesium stearate, or di-calcium phosphate. These unit dosage forms are prepared by intimately mixing the active ingredient with suitable finely-powdered inert ingredients including diluents, fillers, disintegrating agents, and/or binders such that a uniform mixture is obtained. An inert ingredient is one that will not react with the compounds or modulators and which is non-toxic to the animal being treated. Suitable inert ingredients include starch, lactose, talc, magnesium stearate, vegetable gums and oils, and the like. These formulations may contain a widely variable amount of the active and inactive ingredients depending on numerous factors such as the size and type of the animal species to be treated and the type and severity of the infection. The active ingredient may also be administered as an additive to the feed by simply mixing the compound with the feedstuff or by applying the compound to the surface of the feed. Alternatively the active ingredient may be mixed with an inert carrier and the resulting composition may then either be mixed with the feed or fed directly to the animal. Suitable inert carriers include corn meal, citrus meal, fermentation residues, soya grits, dried grains and the like. The active ingredients are intimately mixed with these inert carriers by grinding, stirring, milling, or tumbling such that the final composition contains from 0.001 to 5% by weight of the active ingredient.

The compounds or modulators may alternatively be administered parenterally via injection of a formulation consisting of the active ingredient dissolved in an inert liquid carrier. Injection may be either intramuscular, intraruminal, intratracheal, or subcutaneous. The injectable formulation consists of the active ingredient mixed with an appropriate inert liquid carrier. Acceptable liquid carriers include the vegetable oils such as peanut oil, cotton seed oil, sesame oil and the like as well as organic solvents such as solketal, glycerol formal and the like. As an alternative, aqueous parenteral formulations may also be used. The vegetable oils are the preferred liquid carriers. The formulations are prepared by dissolving or suspending the active ingredient in the liquid carrier such that the final formulation contains from 0.005 to 10% by weight of the active ingredient.

Topical application of the compounds or modulators is possible through the use of a liquid drench or a shampoo containing the instant compounds or modulators as an aqueous solution or suspension. These formulations generally contain a suspending agent such as bentonite and normally will also contain an antifoaming agent. Formulations containing from 0.005 to 10% by weight of the active ingredient are acceptable. Preferred formulations are those containing from 0.01 to 5% by weight of the instant compounds or modulators.

The following examples illustrate the present invention without, however, limiting the same thereto.

EXAMPLE 1

Cloning of Human Histamine H4 Receptor DNA (pH4R)

cDNA Synthesis:

First strand synthesis: Approximately 5 μg of human bone marrow mRNA (Clonetech) was used to synthesize cDNA using the cDNA synthesis kit (Life Technologies). 2 μl of Not 1 primer adapter was added to 5 μl of mRNA and the mixture was heated to 70° C. for 10 minutes and placed on ice. The following reagents were added on ice: 4 μl of 5× first strand buffer (250 mM TRIS-HCl (pH8.3), 375 mM KCl, 15 mM$MgCl_2$), 2 μl of 0.1M DTT, 10 mM dNTP (nucleotide triphosphates) mix and 1 μl of DEPC treated water. The reaction was incubated at 42° C. for 5 minutes. Finally, 5 μl of Superscript RT II was added and incubated at 42° C. for 2 more hours. The reaction was terminated on ice.

Second strand synthesis: The first strand product was adjusted to 93 μl with water and the following reagents were added on ice: 30 μl of 5× 2nd strand buffer (100 mM TRIS-HCl (pH6.9), 450 mM KCl, 23 mM $MgCl_2$, 0.75 mM β-NAD+, 50 mM $(NH_4)_2SO_4$), 3 μl of 10 mM dNTP (nucleotide triphosphates), 1 μl *E. coli* DNA ligase (10units)1 μl RNase H (2units), 4 μl DNA pol I (10 units). The reaction was incubated at 16° C. for 2 hours. The DNA from second strand synthesis was treated with T4 DNA polymerase and placed at 16° C. to blunt the DNA ends. The double stranded cDNA was extracted with 150 μl of a mixture of phenol and chloroform (1:1, v:v) and precipitated with 0.5 volumes of 7.5 M NH4OAc and 2 volumes of absolute ethanol. The pellet was washed with 70% ethanol and dried down at 37° C. to remove the residual ethanol. The double stranded DNA pellet was resuspended in 25 μl of water and the following reagents were added; 10 μl of 5× T4 DNA ligase buffer, 10 μl of Sal1 adapters and 5 μl of T4 DNA ligase. The ingredients were mixed gently and ligated overnight at 16° C. The ligation mix was extracted with phenol:chloroform:isoamyl alcohol, vortexed thoroughly and centrifuged at room temperature for 5 minutes at 14,000×g to separate the phases. The aqueous phase was transferred to a new tube and the volume adjusted to 100 ml with water. The purified DNA was size selected on a chromaspin 1000 column (Clontech) to eliminate the smaller cDNA molecules. The double stranded DNA was digested with Not1 restriction enzyme for 3–4 hours at 37° C. The restriction digest was electrophoresed on a 0.8% low melt agarose gel. The cDNA in the range of 1–5 kb was cut out and purified using Gelzyme (Invitrogen). The product was extracted with phenol:chloroform and precipitated with $NH_4OAc$ and absolute ethanol. The pellet was washed with 70% ethanol and resuspended in 10 ml of water.

Ligation of cDNA to the Vector: The cDNA was split up into 5 tubes (2 μl each) and the ligation reactions were set up by adding 4.5 μl of water, 2 μl of 5× ligation buffer, 1 μl of p-Sport vector DNA (cut with Sal-1/Not1 and phosphatase treated) and 0.5 μl of T4 DNA ligase. The ligation was incubated at 40° C. overnight.

Introduction of Ligated cDNA into *E. coli* by Electroporation:

The ligation reaction volume was adjusted to a total volume of 20 μl with water. Five ml of yeast tRNA, 12.5 ml of 7.5M $NH_4OAc$ and 70 ml of absolute ethanol (−20° C.) was added. The mixture was vortexed thoroughly, and immediately centrifuged at room temperature for 20 minutes at 14,000×g. The pellets were washed in 70% ethanol and each pellet was resuspended in 5 ml of water. All 5 ligations (25 ml) were pooled and 100 μl of DH10B electro-competent cells (Life Technologies) were electroporated with 1 μl of DNA (total of 20 electroporations), then plated out on ampicillin plates to determine the number of recombinants (cfu) per μl. The entire library was seeded into 2 liters of Super Broth and maxipreps were made using Promega Maxi Prep kit and purified on cesium chloride gradients.

Screening of Library:

1 μl aliquots of the library constructed above were electroporated into Electromax DH10B cells (Life Technologies). The volume was adjusted to 1 ml with SOC media and incubated for 1 hour at 37° C. with shaking. The library was then plated out on 50 150 $cm^2$ plates containing LB to a density of 5000 colonies per plate. These were grown overnight at 37° C.

A histamine H4 receptor probe was generated by polymerase chain reaction using the following primer pair. 5' oligo: 5' ACTAGAATTCACCGTGATGCCAGATACTAATAGCACA 3' [SEQ. ID. NO.: 1] and 3' oligo: 5' ATGCAGGATCCAGCATTTGAGACTGACAGGTAT 3' [SEQ. ID. NO.: 2]. Amplification was cycled 35 times with a 50–60° C. annealing temperature and human thalamus cDNA as template. The PCR fragment that was generated (400–500 bp) was 32P-labelled using the klenow fragment of DNA polymerase I and an oligo-labeling kit (Pharmacia). The fragment was then cleaned by one passage through a S-200 column (Pharmacia).

The library colonies are lifted on nitrocellulose filters and cross-linked via UV irradiation (Stratagene). Filters were washed three times in buffer (50 mM TRIS, 1 M NaCl, 2 mM EDTA, 1% SDS) at 42° C. Filters were then prehybridized in 1:1 Southern Prehyb:Formamide with salmon sperm DNA (50 mg, boiled) for 6 hours at 42° C. Filters were then hybridized with the probe ($1\times10^6$ counts/ml) overnight. The filters were then washed one time with 2×SSC/0.2% SDS at room temperature for 15 minutes, 2 times with 0.2×SSC/0.1% SDS at 45° C. for 30 minutes each. Filters were then wrapped in plastic wrap and exposed to film (Kodak) overnight at −80° C.

Positive clones were identified. Resulting positives were cored from the original plate, incubated in LB for 45 minutes at 37° C. and re-plated overnight. The filter lifting/hybridizing/washing/colony picking procedure was replicated until a single clone or clones were isolated, representing an individual cDNA.

From the screen for human histamine H4 receptor, all cDNA clones were isolated and sequenced. One clone, pH4R, contained a 1173 bp insert (FIG. 1). This sequence had an apparent open reading frame from nucleotide 1 to 1173. This open reading frame encoded a protein of 371 amino acids (FIG. 2).

EXAMPLE 2

Cloning of Human Histamine H4 Receptor cDNA into a Mammalian Expression Vector

The human histamine H4 receptor cDNAs (collectively referred to as pH4R) were cloned into the mammalian expression vector pCIneo. The human histamine H4 receptor cDNA clone was isolated from the human thalamus cDNA library. The full length cDNA was used as the template for PCR using specific primers with EcoR1 (5'ACT AGA ATT CGC CAC CAT GCC AGA TAC TAA TAG CACA3') [SEQ. ID. NO.:3] and Not1 (5'ACT ACT GCG GCC GCT TAA GAA GAT ACT GAC CGA CTGT3') [SEQ. ID. NO.:4] sites for cloning. The PCR product was purified on a column (Wizard PCR DNA purification kit from Promega) and digested with Not I and EcoR1 (NEB) to create cohesive ends. The product was purified by a low melting agarose gel electrophoresis. The pCIneo vector was digested with EcoR1 and Not1 enzymes and subsequently purified on a low melt agarose gel. The linear vector was used to ligate to the human histamine H4 receptor cDNA inserts. Recombinants were isolated, designated human histamine H4 receptor, and used to transfect mammalian cells (SK-N-MC cells) by $CaPO_4$-DNA precipitation. Stable cell clones were selected by growth in the presence of G418. Single G418 resistant clones were isolated and shown to contain the intact human histamine H4 receptor gene. Clones containing the human histamine H4 receptor cDNAs were analyzed for pH4R expression by measuring inhibition of adenylate cyclase in response to histamine according to the method of (Konig, Mahan et al. 1991) or by directly measuring cAMP accumulation by radioimmunoassay using Flashplates (NEN). Expression was also analyzed using [$^3$H]-histamine binding assays (Clark, Korte et al. 1992). Recombinant plasmids containing human histamine H4 receptor encoding DNA were used to transform the mammalian COS7 or CHO cells or HEK293 or L-cells or SK-N-MC cells.

Cells expressing human histamine H4 receptor, stably or transiently, are used to test for expression of human histamine H4 receptor and for [$^3$H]-histamine binding activity (FIG. 4). These cells are used to identify and examine other compounds for their ability to modulate, inhibit or activate the human histamine H4 receptor and to compete for radioactive histamine binding.

Cassettes containing the human histamine H4 receptor cDNA in the positive orientation with respect to the promoter are ligated into appropriate restriction sites 3' of the promoter and identified by restriction site mapping and/or sequencing. These cDNA expression vectors are introduced into fibroblastic host cells for example COS-7 (ATCC# CRL1651), and CV-1 tat [Sackevitz et al., Science 238: 1575 (1987)], 293, L (ATCC# CRL6362), SK-N-MC (ATCC# HTB-10) by standard methods including but not limited to electroporation, or chemical procedures (cationic liposomes, DEAE dextran, calcium phosphate). Transfected cells and cell culture supernatants are harvested and analyzed for human histamine H4 receptor expression as described herein.

All of the vectors used for mammalian transient expression can be used to establish stable cell lines expressing human histamine H4 receptor. Unaltered human histamine H4 receptor cDNA constructs cloned into expression vectors are expected to program host cells to make human histamine H4 receptor protein. The transfection host cells include, but are not limited to, CV-1-P [Sackevitz et al., Science 238: 1575 (1987)], tk-L [Wigler, et al. Cell 11: 223 (1977)], NS/0, and dHFr-CHO [Kaufman and Sharp, J. Mol. Biol. 159: 601, (1982)].

Co-transfection of any vector containing human histamine H4 receptor cDNA with a drug selection plasmid including, but not limited to G418, aminoglycoside phosphotransferase; hygromycin, hygromycin-B phosphotransferase; APRT, xanthine-guanine phosphoribosyl-transferase, will allow for the selection of stably transfected clones. Levels of human histamine H4 receptor are quantitated by the assays described herein.

Human histamine H4 receptor cDNA constructs are also ligated into vectors containing amplifyable drug-resistance markers for the production of mammalian cell clones synthesizing the highest possible levels of human histamine H4 receptor. Following introduction of these constructs into cells, clones containing the plasmid are selected with the appropriate agent, and isolation of an over-expressing clone with a high copy number of plasmids is accomplished by selection in increasing doses of the agent.

The expression of recombinant human histamine H4 receptor is achieved by transfection of full-length human histamine H4 receptor cDNA into a mammalian host cell.

Characterization of Human Histamine H4 Receptor

Human SK-N-MC cells were transfected with pH4R and selected in the presence of neomycin for 10 days. Individual colonies were picked and grown in 6-well dishes. Cells were then plated onto 96-well plates and grown to confluence. Cells were incubated for 20 minutes with isobutylmethylxanthine (1 mM). Cells were then stimulated with histamine (100 pM–100 uM) for 5 minutes. Cells were then stimulated with forskolin (3 uM) and allowed to incubate at 37° C. for 20 minutes. Cells were then treated with 0.1N hydrochloric acid. Cells were then frozen and thawed. Aliquots of the supernatant were then analyzed for their cyclic AMP content using a standard cAMP radioimmunoassay kit (Flashplates, NEN). The forskolin treatment raises the intracellular concentration of cAMP. Any cells that responded to histamine by decreasing the cAMP content in response to forskolin were considered to be expressing active functional human histamine H4 receptor. The recombinant human histamine H4 receptor expressed from the human histamine H4 receptor-encoding DNA molecule described herein was shown to be specifically activated by histamine.

EXAMPLE 3

Binding Assay on Recombinant Human Histamine H4 Receptor

SK-N-MC cells or COS7 cells that were transiently transfected with pH4R and grown in 150 cm2 tissue culture dishes. Cells were washed with saline solution, scraped with a cell scraper and collected by centrifugation (1000 rpm, 5 min). SK-N-MC or COS7 cells expressing human histamine H4 receptor binds $^{3}$H-histamine with high affinity (FIG. 4). Cell membranes are prepared by homogenization of the cell pellet in 20 mM Tris-HCl with a polytron tissue homogenizer for 10 seconds at high speed. Homogenate is centrifuged at 1000 rpm for 5 minutes at 4° C. The supernatant is then collected and centrifuged at 20,000×g for 25 minutes at 4° C. The final pellet is resuspended in 50 mM Tris-HCl. Cell membranes are incubated with $^{3}$H-histamine (0.5 nM–70 nM) in the presence or absence of excess histamine (10000 nM). Incubation occurs at room temperature for 45 minutes. Membranes are harvested by rapid filtration over Whatman GF/C filters and washed 4 times with ice cold 50 mM Tris HCl. Filters are then dried, mixed with scintillant and counted for radioactivity. SK-N-MC or COS7 cells expressing human histamine H4 receptor are used to measure the affinity of binding of other compounds and their ability to displace $^{3}$H-ligand binding by incubating the above described reaction in the presence of various concentrations of inhibitor or compound to be tested.

EXAMPLE 4

Primary Structure of the Human Histamine H4 Receptor Protein

The nucleotide sequences of pH4R receptor revealed a single large open reading frame of about 1173 base pairs. The first in-frame methionine was designated as the initiation codon for an open reading frame that predicts a human histamine H4 receptor protein with an estimated molecular mass ($M_r$) of about 44495.

The predicted human histamine H4 receptor protein was aligned with nucleotide and protein databases and found to be related to the human histamine H1, human histamine H2 receptors, and human histamine H3 receptors. Approximately 25% of the amino acids in human histamine H4 receptor were highly conserved, showing at least 25% amino acid identity within the histamine H2 receptor, 28% with the histamine H1 receptor, 38% with the human H3 receptor, and approximately 25% with the family of biogenic amine G-protein coupled receptors. The conserved motifs found in this family of receptors, such as seven conserved hydrophobic domains, were also found in the human histamine H4 receptor sequence. The human histamine H4 receptor protein contained the conserved aspartate residue found in the 3$^{rd}$ transmembrane domain of all biogenic amine receptors. The human histamine H4 receptor protein contained the conserved asparagine residue found in the 1$^{st}$ transmembrane domain of all biogenic amine receptors. The human histamine H4 receptor protein contained the conserved arginine residue found in the 3$^{rd}$ transmembrane domain of all biogenic amine receptors. The human histamine H4 receptor protein contained the conserved tryptophan residue found in the 4$^{th}$ transmembrane domain of all biogenic amine receptors. The human histamine H4 receptor protein contained the conserved phenylalanine residue found in the 5$^{th}$ transmembrane domain of all biogenic amine receptors. The human histamine H4 receptor protein contained the conserved pro-line residue found in the $6^{th}$ transmembrane domain of all biogenic amine receptors. The human histamine H4 receptor protein contained the conserved tyrosine residue found in the $7^{th}$ transmembrane domain of all biogenic amine receptors.

EXAMPLE 5

Cloning of the Human Histamine H4 Receptor cDNA into *E. coli* Expression Vectors Recombinant human histamine H4 receptor is produced in *E. coli* following the transfer of the human histamine H4 receptor expression cassette into *E. coli* expression vectors, including but not limited to, the pET series (Novagen). The pET vectors place human histamine H4 receptor expression under control of the tightly regulated bacteriophage T7 promoter. Following transfer of this construct into an *E. coli* host which contains a chromosomal copy of the T7 RNA polymerase gene driven by the inducible lac promoter, expression of human histamine H4 receptor is induced when an appropriate lac substrate (IPTG) is added to the culture. The levels of expressed human histamine H4 receptor are determined by the assays described herein.

The cDNA encoding the entire open reading frame for human histamine H4 receptor is inserted into the NdeI site of pET [16]11*a*. Constructs in the positive orientation are identified by sequence analysis and used to transform the expression host strain BL21. Transformants are then used to inoculate cultures for the production of human histamine H4 receptor protein. Cultures may be grown in M9 or ZB media, whose formulation is known to those skilled in the art. After growth to an $OD_{600}$=1.5, expression of human histamine H4 receptor is induced with 1 mM IPTG for 3 hours at 37° C.

EXAMPLE 6

Cloning of Human Histamine H4 Receptor cDNA into a Baculovirus Expression Vector for Expression in Insect Cells Baculovirus vectors, which are derived from the genome of the AcNPV virus, are designed to provide high level expression of cDNA in the Sf9 line of insect cells (ATCC CRL# 1711). Recombinant baculovirus expressing human histamine H4 receptor cDNA is produced by the following standard methods (In Vitrogen Maxbac Manual): the human histamine H4 receptor cDNA constructs are ligated into the polyhedrin gene in a variety of baculovirus transfer vectors, including the pAC360 and the BlueBac vector (In Vitrogen). Recombinant baculovirus are generated by homologous recombination following co-transfection of the baculovirus transfer vector and linearized AcNPV genomic DNA [Kitts, P. A., Nuc. Acid. Res. 18: 5667 (1990)] into Sf9 cells. Recombinant pAC360 viruses are identified by the absence of inclusion bodies in infected cells and recombinant pBlueBac viruses are identified on the basis of β-galactosidase expression (Summers, M. D. and Smith, G. E., Texas Agriculture Exp. Station Bulletin No. 1555). Following plaque purification, human histamine H4 receptor expression is measured by the assays described herein.

The cDNA encoding the entire open reading frame for human histamine H4 receptor is inserted into the BamHI site of pBlueBacII. Constructs in the positive orientation are identified by sequence analysis and used to transfect Sf9 cells in the presence of linear AcNPV mild type DNA.

Authentic, active human histamine H4 receptor is found in the cytoplasm of infected cells. Active human histamine H4 receptor is extracted from infected cells by hypotonic or detergent lysis.

EXAMPLE 7

Cloning of Human Histamine H4 receptor cDNA into a Yeast Expression Vector

Recombinant human histamine H4 receptor is produced in the yeast *S. cerevisiae* following the insertion of the optimal human histamine H4 receptor cDNA cistron into expression vectors designed to direct the intracellular or extracellular expression of heterologous proteins. In the case of intracellular expression, vectors such as EmBLyex4 or the like are ligated to the human histamine H4 receptor cistron [Rinas, U. et al., Biotechnology 8: 543–545 (1990); Horowitz B. et al., J. Biol. Chem. 265: 4189–4192 (1989)]. For extracellular expression, the human histamine H4 receptor cistron is ligated into yeast expression vectors which fuse a secretion signal (a yeast or mammalian peptide) to the $NH_2$ terminus of the human histamine H4 receptor protein [Jacobson, M. A., Gene 85: 511–516 (1989); Riett L. and Bellon N. Biochem. 28: 2941–2949 (1989)].

These vectors include, but are not limited to pAVE1>6, which fuses the human serum albumin signal to the expressed cDNA [Steep O. Biotechnology 8: 42–46 (1990)], and the vector pL8PL which fuses the human lysozyme signal to the expressed cDNA [Yamamoto, Y., Biochem. 28: 2728–2732)]. In addition, human histamine H4 receptor is expressed in yeast as a fusion protein conjugated to ubiquitin utilizing the vector pVEP [Ecker, D. J., J. Biol. Chem. 264: 7715–7719 (1989), Sabin, E. A., Biotechnology 7: 705–709 (1989), McDonnell D. P., Mol. Cell Biol. 9: 5517–5523 (1989)]. The levels of expressed human histamine H4 receptor are determined by the assays described herein.

EXAMPLE 8

Cloning Murine, Rat, and Guinea Pig Histamine H4 Receptor cDNAs

Two primers, forward primer: 5'GTG GTG GAC AAA AAC CTT AGA CAT CGA AGT3' [SEQ. ID. NO.:11], and reverse primer: 5'ACT GAG ATG ATC ACG CTT CCA CAG GCT CCA3' (SEQ. ID. NO.:12 were used to amplify a 500 bp cDNA fragment from mouse spleen, rat spleen, and guinea pig bone marrow cDNA libraries. These cDNA fragments were sub-cloned into the pPCR2 vector (Invitrogen). The resulting DNA sequence showed 65–70% identity to human H4 sequence and this region of each clone was used as anchoring regions to clone the 5' and 3' ends by RACE methodology.

Cloning of Mouse H4 Full Length cDNA

The mouse H4 cDNA 5' end was PCR amplified by the rapid amplification of cDNA end (RACE) method from mouse spleen Marathron-Ready cDNA (Clontech) using the adaptor primer (AP): 5'CCA TCC TAA TAC GAC TCA CTA TAG GGC 3' [SEQ. ID. NO.:13] and mouse gene specific primer P1: 5'CAC TCT GTA ACA AAG CCA GGC TCA CAG TC 3' [SEQ. ID. NO.:14]. The mouse H4 cDNA 3' end was RACE amplified from mouse spleen Marathron-Ready cDNA (Clontech) using the AP and mouse H4 specific gene primer P2: 5' TGC ATC TCG TCA CTC AGA AAG TCC TCG AAG 3'[SEQ. ID. NO.:15]. The 5' end and 3' end RACE products of mouse histamine H4 receptor cDNA were sequenced and the complete cDNA sequence assembled. The coding region of mouse H4 was then PCR amplified from mouse spleen cDNA using two primers, forward primer: 5' ACG AGA ATT CGC CAC CAT GTC GGA GTC TAA CAG TAC TGG 3' [SEQ. ID. NO.:16] and reverse primer: 5' ATG ACA GCG GCC GCA GTT GGC ACT CGT GAA GCA ATT CTC 3' [SEQ. ID. NO.:17]. The full-length cDNA PCR product was cloned into the mammalian expression vector pCINeo (Promega).

Cloning of Rat H4 cDNA.

Similar to that of mouse, the rat histamine H4 receptor cDNA 5' and 3' ends were cloned by RACE from a rat spleen cDNA library (Marathon-Ready cDNA-Clonetech) using P3: 5'CAT TGG GCC ATT GAC CAA GAA AGC CAG TAT C3' [SEQ. ID. NO.:18] and P4: 5' TCA TTC AGA AAG TCC ACG AGG AAA GAG CAG 3' [SEQ. ID. NO.:19] together with the primer AP, described supra. The RACE cDNA product was sequenced and the complete cDNA sequence assembled. The coding region of rat histamine H4 receptor was PCR amplified from the rat spleen cDNA library using two primers, forward primer: 5' ACG TGA ATT CGC CAC CAT GTC GGA GTC TAA CGG CAC TGA 3' [SEQ. ID. NO.:20] and reverse primer: 5' ACT GAT GCG GCC GCG AAG CTG GCA CAC ATG AAG CTT CTC 3' [SEQ. ID. NO.:21]. The full-length cDNA product was cloned into the mammalian expression vector pCINeo.

Cloning the Guinea Pig H4 cDNA Full Length

Guinea pig bone marrow RNA was purified using a RNA purification kit Trizol (Gibco-BRL) and cDNA first strand was synthesized using the smart cDNA synthesis system (Clontech) per the manufacture's instructions. This cDNA library was used to clone the guinea pig histamine H4 receptor 5' end and 3' end by RACE methodology using guinea pig H4 specific primers P5: 5' ATA ATG ATG TAG GGA GAG CAA AGT ACC ACT 3' [SEQ. ID. NO.:22] and P6: 5' ACA CTC CTG CAG ACA GGA CCC CGA TTC AAG 3' [SEQ. ID. NO.:23] together with the adaptor primer provided by the manufacturer. The race products were sequenced and the complete cDNA sequence assembled. The complete coding region of guinea pig histamine H4 receptor was then PCR amplified from the bone marrow cDNA pool using two primers: forward primer: 5' ACG TCT CGA GGC CAC CAT GTT GGC AAA TAA CAG TAC AAT CG 3' [SEQ. ID. NO.:24] and reverse primer: 5' ACG ACA GCG GCC GCC TTC AAG TGG ATA TTG AGC GGT TGT GT 3' [SEQ. ID. NO.:25]. The full-length cDNA clone was cloned into the mammalian expression vector pCINeo.

The complete polynucleotide coding sequence for murine, rat, and guinea pig are shown in FIG. 5. The corresponding amino acid sequences are shown in FIG. 6, the alignment of human, murine, rat, and guinea pig polynucleotides are shown in FIG. 7, and the alignment of human, murine, rat, and guinea pig polypeptides are shown in FIG. 8. The percent homology between the human, rat, guinea pig and mouse nucleotide sequences was determined using Vector NTI Suite 6.0 (Informatix, Inc.), and the results are shown in Table 1.

TABLE 1

| | Human | Murine | Rat | Guinea Pig |
|---|---|---|---|---|
| Human | 100 | 72.8 | 72.5 | 75.6 |
| Murine | | 100 | 88.4 | 75.3 |

TABLE 1-continued

| | Human | Murine | Rat | Guinea Pig |
|---|---|---|---|---|
| Rat | | | 100 | 74.5 |
| Guinea Pig | | | | 100 |

EXAMPLE 9

Ligand Binding to Mammalian Histamine H4 Receptors

The affinity of $^3$H-histamine for rat, mouse, guinea pig, and human histamine H4 receptors was determined using standard techniques as described herein. Saturation binding was performed on membranes from SK-N-MC cells stably transfected with the appropriate histamine H4 receptor. The Kd values were derived from a −1/slope of the linear regression of a Scatchard plot (bound/free vs bound). The results are show in Table 2.

TABLE 2

| Species | $^3$H-histamine $K_d$ (nM) |
|---|---|
| Rat | 105 |
| Murine | 34 |
| Guinea Pig | 20 |
| Human | 5 |

The relative affinity of several known histamine receptor ligands was determined by competitive binding of 30 nM $^3$H-histamine. $K_i$ values for each ligand were calculated according to the method of Cheng and Pruscoff ($K_i$=$IC_{50}$/(1+[$^3$H-histamine]/$K_d$)). The Kd values for $^3$H-histamine were those set forth in Table 2. The results are presented in Table 3.

TABLE 3

| Compound | Human Ki (nM) | Guinea Pig Ki (nM) | Rat Ki (nM) | Murine Ki (nM) |
|---|---|---|---|---|
| Imetit | 1.3 | 30 | 6.8 | 6.6 |
| Histamine | 5.9 | 27 | 70 | 41 |
| Clobenpropit | 4.9 | 3.6 | 63 | 14 |
| N-methylhistamine | 48 | 220 | 552 | 303 |
| Thioperamide | 52 | 83 | 28 | 22 |
| R-α-methylhistamine | 144 | 486 | 698 | 382 |
| Burimamide | 124 | 840 | 958 | 696 |
| Clozapine | 626 | 185 | 2200 | 2780 |

EXAMPLE 10

RT-PCR Detection of Human H4 mRNA Expression.

PCR primers were used to expand a human Histamine H4 receptor cDNA fragment in cDNA libraries of cerebellum, cortex, hypothalamus, small intestine, dorsal root ganglia (DRG), hippocampus, spleen, thalamus, placenta, heart, liver, lung, uterus, pituitary, spinal cord, and bone marrow under condition of 94 C 45 sec, 60 C 45 sec, 72 C 2 min for 35 cycles. The PCR products were run on a 1% agarose gel and DNA was stained with ethidium bromide (10 ug/ml) and visualized with UV. The PCR products in gel were then transferred to a nitrocellulose membrane and hybridized with a $^{32}$P-labeled human H4 DNA probe. As seen in FIG. 3, the human Histamine H4 receptor is highly expressed in the bone marrow. Similar experiments were conducted for mouse, rat, and guinea pig histamine H4 receptor. In all species, the histamine H4 receptor is highly expressed in the bone marrow.

REFERENCES

Arrang, J. M., M. Garbarg, et al. (1983). "Autoinhibition of brain histamine release mediated by a novel class (H3) of histamine receptor." *Nature* (*London*) 302(5911): 832–7.

Clark, M. A., A. Korte, et al. (1993). "Guanine nucleotides and pertussis toxin reduce the affinity of histamine H3 receptors on AtT-20 cells." *Agents Actions* 40(3–4): 129–34.

Clark, M. A., A. Korte, et al. (1992). "High affinity histamine H3 receptors regulate ACTH release by AtT-20 cells." *Eur. J. Pharmacol.* 210(1): 31–5.

De Vos, C. (1999). "H1-receptor antagonists: Effects on leukocytes, myth or reality." Clin. Exp. Allergy 29(Suppl.3): 60–63.

Gantz, L, M. Schaffer, et al. (1991). "Molecular cloning of a gene encoding the histamine H2 receptor." *Proc. Natl. Acad. Sci. U.S.A.* 88(2): 429–33.

Hill, S. J., C. R. Ganellin, et al. (1997). "International Union of Pharmacology. XIII. Classification of histamine receptors." *Pharmacol. Rev.* 49(3): 253–278.

Konig, M., L. C. Mahan, et al. (1991). "Method for identifying ligands that bind to cloned Gs- or Gi-coupled receptors." *Mol. Cell. Neurosci.* 2(4): 331–7.

Luvenberg, T. W., B. L. Roland, et al. (1999) "Cloning and functional expression of the human histamine H3 receptor." *Mol. Pharmacology* 55: 1101–1107.

Pollard, H., J. Moreau, et al. (1993). "A detailed autoradiographic mapping of histamine H3 receptors in rat brain areas." *Neuroscience* (*Oxford*) 52(1): 169–89.

Raible, D. G., Lenahan, T., et al. (1994) "Pharmacologic characterization of a novel histamine receptor on human eosinophils." *Am. J. Respir. Crit. Care Med.* 149: 1506–1511

Yamashita, M., H. Fukui, et al. (1991). "Expression cloning of a cDNA encoding the bovine histamine H1 receptor." *Proc. Natl. Acad. Sci. U.S.A.* 88(24): 11515–19.

What is claimed is:

1. An isolated and purified nucleic acid molecule that encodes a guinea pig histamine H4 receptor protein, or a complement of said nucleic acid molecule, comprising a member selected from the group consisting of:

(a) a polynucleotide sequence encoding a polypeptide comprising amino acids 1 to 389 of SEQ ID NO: 10; and (b) a polynucleotide sequence which is a full-length complement of a polynucleotide sequence encoding amino acids 1 to 389 of SEQ ID NO: 10.

2. The nucleic acid molecule of claim 1 wherein the polynucleotide is RNA.

3. The nucleic acid molecule of claim 1 wherein the polynucleotide is DNA.

4. The nucleic acid molecule of claim 1, having the nucleotide sequence SEQ ID NO:7.

5. An expression vector for expression of a guinea pig histamine H4 receptor protein in a recombinant host, wherein said vector contains a nucleic acid sequence encoding a guinea pig histamine H4 receptor protein having the amino acid sequence of SEQ ID NO:10.

6. The expression vector of claim 5, wherein the expression vector contains a nucleic acid molecule having the nucleotide sequence SEQ ID NO:7.

7. A recombinant host cell containing a recombinantly cloned nucleic acid molecule encoding a guinea pig histamine H4 receptor protein having the amino acid sequence of SEQ ID NO:10.

8. The recombinant host cell of claim 7, wherein said nucleic acid molecule has the nucleotide sequence of SEQ ID NO:7.

9. A process for expression of guinea pig histamine H4 receptor protein in a recombinant host cell, comprising:

(a) transferring an expression vector containing a nucleic acid sequence encoding a guinea pig histamine H4 receptor protein having the amino acid sequence of SEQ ID NO: 10 into suitable host cells; and (b) culturing the host cells of step (a) under conditions which allow expression of the guinea pig histamine H4 receptor protein from the expression vector.

* * * * *

SEQUENCE LISTING

```
<160> NUMBER OF SEQ ID NOS: 27

<210> SEQ ID NO 1
<211> LENGTH: 1173
<212> TYPE: DNA
<213> ORGANISM: Homo sapiens

<400> SEQUENCE: 1

atgccagata ctaatagcac aatcaattta tcactaagca ctcgtgttac tttagcattt     60

tttatgtcct tagtagcttt tgctataatg ctaggaaatg ctttggtcat tttagctttt    120

gtggtggaca aaaaccttag acatcgaagt agttattttt ttcttaactt ggccatctct    180

gacttctttg tgggtgtgat ctccattcct ttgtacatcc ctcacacgct gttcgaatgg    240

gattttggaa aggaaatctg tgtattttgg ctcactactg actatctgtt atgtacagca    300

tctgtatata acattgtcct catcagctat gatcgatacc tgtcagtctc aaatgctgtg    360

tcttatagaa ctcaacatac tggggtcttg aagattgtta ctctgatggt ggccgtttgg    420

gtgctggcct tcttagtgaa tgggccaatg attctagttt cagagtcttg gaaggatgaa    480

ggtagtgaat gtgaacctgg atttttttcg gaatggtaca tccttgccat cacatcattc    540

ttggaattcg tgatcccagt catcttagtc gcttatttca acatgaatat ttattggagc    600

ctgtggaagc gtgatcatct cagtaggtgc caaagccatc ctggactgac tgctgtctct    660

tccaacatct gtggacactc attcagaggt agactatctt caaggagatc tctttctgca    720

tcgacagaag ttcctgcatc ctttcattca gagagacaga ggagaaagag tagtctcatg    780

ttttcctcaa gaaccaagat gaatagcaat acaattgctt ccaaaatggg ttccttctcc    840

caatcagatt ctgtagctct tcaccaaagg gaacatgttg aactgcttag agccaggaga    900

ttagccaagt cactggccat tctcttaggg gtttttgctg tttgctgggc tccatattct    960

ctgttcacaa ttgtcctttc attttattcc tcagcaacag gtcctaaatc agtttggtat   1020

agaattgcat tttggcttca gtggttcaat tcctttgtca atcctctttt gtatccattg   1080

tgtcacaagc gctttcaaaa ggctttcttg aaaatatttt gtataaaaaa gcaacctcta   1140

ccatcacaac acagtcggtc agtatcttct taa                                1173
```

-continued

<210> SEQ ID NO 2
<211> LENGTH: 390
<212> TYPE: PRT
<213> ORGANISM: Homo sapiens

<400> SEQUENCE: 2

```
Met Pro Asp Thr Asn Ser Thr Ile Asn Leu Ser Leu Ser Thr Arg Val
1               5                   10                  15

Thr Leu Ala Phe Phe Met Ser Leu Val Ala Phe Ala Ile Met Leu Gly
            20                  25                  30

Asn Ala Leu Val Ile Leu Ala Phe Val Val Asp Lys Asn Leu Arg His
        35                  40                  45

Arg Ser Ser Tyr Phe Phe Leu Asn Leu Ala Ile Ser Asp Phe Phe Val
    50                  55                  60

Gly Val Ile Ser Ile Pro Leu Tyr Ile Pro His Thr Leu Phe Glu Trp
65                  70                  75                  80

Asp Phe Gly Lys Glu Ile Cys Val Phe Trp Leu Thr Thr Asp Tyr Leu
                85                  90                  95

Leu Cys Thr Ala Ser Val Tyr Asn Ile Val Leu Ile Ser Tyr Asp Arg
            100                 105                 110

Tyr Leu Ser Val Ser Asn Ala Val Ser Tyr Arg Thr Gln His Thr Gly
        115                 120                 125

Val Leu Lys Ile Val Thr Leu Met Val Ala Val Trp Val Leu Ala Phe
    130                 135                 140

Leu Val Asn Gly Pro Met Ile Leu Val Ser Glu Ser Trp Lys Asp Glu
145                 150                 155                 160

Gly Ser Glu Cys Glu Pro Gly Phe Phe Ser Glu Trp Tyr Ile Leu Ala
                165                 170                 175

Ile Thr Ser Phe Leu Glu Phe Val Ile Pro Val Ile Leu Val Ala Tyr
            180                 185                 190

Phe Asn Met Asn Ile Tyr Trp Ser Leu Trp Lys Arg Asp His Leu Ser
        195                 200                 205

Arg Cys Gln Ser His Pro Gly Leu Thr Ala Val Ser Ser Asn Ile Cys
    210                 215                 220

Gly His Ser Phe Arg Gly Arg Leu Ser Ser Arg Arg Ser Leu Ser Ala
225                 230                 235                 240

Ser Thr Glu Val Pro Ala Ser Phe His Ser Glu Arg Gln Arg Arg Lys
                245                 250                 255

Ser Ser Leu Met Phe Ser Ser Arg Thr Lys Met Asn Ser Asn Thr Ile
            260                 265                 270

Ala Ser Lys Met Gly Ser Phe Ser Gln Ser Asp Ser Val Ala Leu His
        275                 280                 285

Gln Arg Glu His Val Glu Leu Leu Arg Ala Arg Arg Leu Ala Lys Ser
    290                 295                 300

Leu Ala Ile Leu Leu Gly Val Phe Ala Val Cys Trp Ala Pro Tyr Ser
305                 310                 315                 320

Leu Phe Thr Ile Val Leu Ser Phe Tyr Ser Ser Ala Thr Gly Pro Lys
                325                 330                 335

Ser Val Trp Tyr Arg Ile Ala Phe Trp Leu Gln Trp Phe Asn Ser Phe
            340                 345                 350

Val Asn Pro Leu Leu Tyr Pro Leu Cys His Lys Arg Phe Gln Lys Ala
        355                 360                 365

Phe Leu Lys Ile Phe Cys Ile Lys Lys Gln Pro Leu Pro Ser Gln His
```

-continued 370 375 380

Ser Arg Ser Val Ser Ser
385 390

<210> SEQ ID NO 3
<211> LENGTH: 37
<212> TYPE: DNA
<213> ORGANISM: Artificial Sequence
<220> FEATURE:
<223> OTHER INFORMATION: Oligonucleotide Primer

<400> SEQUENCE: 3
actagaattc gccaccatgc cagatactaa tagcaca 37

<210> SEQ ID NO 4
<211> LENGTH: 37
<212> TYPE: DNA
<213> ORGANISM: Artificial Sequence
<220> FEATURE:
<223> OTHER INFORMATION: Oligonucleotide Primer

<400> SEQUENCE: 4
actactgcgg ccgcttaaga agatactgac cgactgt 37

<210> SEQ ID NO 5
<211> LENGTH: 1176
<212> TYPE: DNA
<213> ORGANISM: Mus musculus

<400> SEQUENCE: 5
atgtcggagt ctaacagtac tggcatcttg ccaccagctg ctcaggtccc cttggcattt 60
ttaatgtctt catttgcctt tgctataatg gtaggcaatg ctgtggtcat cttagccttt 120
gtggtggaca gaaaccttag acatcgaagt aattattttt ttcttaattt ggctatttct 180
gacttcctcg tgggtttgat ttccattcct ctgtacatcc ctcacgtgtt gtttaactgg 240
aattttggaa gtggaatctg catgttttgg ctcattactg actatctttt gtgcaccgca 300
tctgtctaca atattgtcct cattagctac gatcgatacc agtcagtttc aaatgctgtg 360
tcttataggg ctcaacacac tggcatcatg aagattgttg ctcaaatggt ggctgtttgg 420
atactggctt tcttggtaaa tggcccgatg attctggctt cagattcttg gaagaacagc 480
acgaacacaa aggactgtga gcctggcttt gttacagagt ggtacatcct caccattaca 540
atgctcttgg aattcctgct tcctgtcatc tctgtggctt atttcaatgt acagatttac 600
tggagcctgt ggaagcgtag ggctctcagt aggtgcccta gccatgctgg attctccact 660
acctcttcca gtgcttcagg acacttacac agagctgggg tggcttgcag gacaagtaat 720
cctggattga aggaatcagc tgcatctcgt cactcagaaa gtcctcgaag aaagagcagc 780
atcctggtgt ccttaaggac tcacatgaac agcagtatca ctgccttcaa agtgggttcc 840
ttctggcgat cggaaagtgc agcgcttcgc caaagggagt acgcagagct tctcagaggc 900
aggaagctag ccaggtcact ggccatcctt ctgagcgctt ttgccatttg ctgggctcca 960
tactgtctgt tcacaattgt cctttcaact taccccagaa cggaacgccc caaatcggtg 1020
tggtacagca ttgccttctg gctgcaatgg ttcaattcgt ttgttaatcc ctttctgtac 1080
cctttgtgtc acaggcgttt ccagaaggct ttctggaaga tactttgtgt gacaaagcaa 1140
ccagcgctgt cacagaacca gtcagtatct tcttga 1176

<210> SEQ ID NO 6

-continued

<211> LENGTH: 1176
<212> TYPE: DNA
<213> ORGANISM: Rattus rattus

<400> SEQUENCE: 6
atgtcggagt ctaacggcac tgacgtcttg ccactgactg ctcaagtccc cttggcattt 60
ttaatgtccc tgcttgcttt tgctataacg ataggcaatg ctgtggtcat tttagccttt 120
gtagcagaca gaaaccttag acatcgaagt aattattttt ttcttaattt ggctatttct 180
gacttcttcg tgggtgtcat ctccattcct ctgtacatcc ctcacacgct gtttaactgg 240
aattttggaa gtggaatctg catgttttgg ctcattactg actatctttt gtgcacagca 300
tccgtctaca gtattgtcct cattagctac gatcgatacc agtcagtttc aaacgctgtg 360
cgttatagag cacagcacac tggcatcctg aaaattgttg ctcaaatggt ggctgtttgg 420
atactggctt tcttggtcaa tggcccaatg attctggctt cggattcttg gaagaacagc 480
accaacacag aggagtgcga gcctggcttt gttactgagt ggtacatcct cgccattaca 540
gcattcttgg aattcctgct ccctgtctcc ttggtggtct atttcagtgt acagatttac 600
tggagcctgt ggaagcgtgg gagtctcagt aggtgcccta gccacgctgg attcatcgct 660
acctcttcca ggggcactgg acactcacgc agaactgggt tggcttgtag gacaagtctt 720
cctggattaa aggaaccagc cgcatccctt cattcagaaa gtccacgagg aaagagcagt 780
ctcctggtgt ccttaaggac tcacatgagc ggtagtatca tcgccttcaa agtgggttcc 840
ttctgccgat cagaaagccc agtgcttcac cagagagagc acgtggagct tctcagaggc 900
aggaagctag ccaggtcgct agctgtcctc ctgagtgctt ttgccatttg ctgggctccg 960
tattgcctgt tcacaattgt tctttcaact tatcgcagag gggagcgccc caaatcgatt 1020
tggtacagca tagccttttg gctacagtgg ttcaattcac ttattaatcc ctttctatac 1080
cctttgtgcc acagacgttt ccagaaggct ttctggaaga tactctgtgt gacaaagcaa 1140
ccagcacctt cacagaccca gtcagtatct tcttga 1176

<210> SEQ ID NO 7
<211> LENGTH: 1170
<212> TYPE: DNA
<213> ORGANISM: Cavia porcellus

<400> SEQUENCE: 7
atgttggcaa ataacagtac aatcgcctta acatcaatta aaatttcttt gacattttta 60
atgtctttac tagctattgc tataatgtta ggcaatgtcg tggtcatttt agcttttatt 120
gtggacagaa atcttagaca tcgaagtaat tacttttttc ttaacttggc cattgcagac 180
ttctttgtgg gtgcaattgc aattcctctg tacatacctt cctcgctgac ttactggact 240
tctggaaagc aagcttgtgt attttggctc attactgact atcttttatg tacagcatct 300
gtgtataata ttgtcctcat cagctacgat cgctaccagt cagtctcaaa tgccgtgtgg 360
tatagagctc agcactctgg cacctggaaa attgctactc agatggtggc tgtttggata 420
ttctccttca tgacaaatgg gccgatgatt ctgatttcag actcttggca gaatagcact 480
acagaatgtg aacctggatt tttaaaaaag tggtactttg ctctccctac atcattattg 540
gaattcctga tccccatctt gttagttgct tatttcagcg cccatattta ctggagcctg 600
tggaagcgag agaaactgag caggtgcctc agccaccctg tactcccctc tgactcttcc 660
agcagtgacc acggacactc ctgcagacag gaccccgatt caagggcgac tctgccagca 720
cggaaagaaa caactgcctc tcttggttca gacaagtcac ggagaaagag cagtctcttg 780

-continued

```
ttttccataa gagcctacaa gaacagcaat gtgatcgctt ccaaaatggg cttcctctcc    840

cactcagatt ccctggctct tcagcaaagg gaacatatcg aacttttcag agccaggaaa    900

ttagccaagt cactggccat actcttagca gcttttgcca tttgctgggc tccatattca    960

ctgactacag ttatctactc attttttcct gaaaggaact tgactaaatc aacctggtac   1020

catactgcct tttggctcca gtggttcaat tcctttgtta atcccttttt gtatccattg   1080

tgtcacaaac gttttcagaa ggctttcctg aaaatacttc ctgtgagaag gcaatccacg   1140

ccaccacaca accgctcaat atccacttga                                    1170
```

<210> SEQ ID NO 8
<211> LENGTH: 391
<212> TYPE: PRT
<213> ORGANISM: Mus musculus

<400> SEQUENCE: 8

```
Met Ser Glu Ser Asn Ser Thr Gly Ile Leu Pro Pro Ala Ala Gln Val
1               5                   10                  15

Pro Leu Ala Phe Leu Met Ser Ser Phe Ala Phe Ala Ile Met Val Gly
            20                  25                  30

Asn Ala Val Val Ile Leu Ala Phe Val Val Asp Arg Asn Leu Arg His
        35                  40                  45

Arg Ser Asn Tyr Phe Phe Leu Asn Leu Ala Ile Ser Asp Phe Leu Val
    50                  55                  60

Gly Leu Ile Ser Ile Pro Leu Tyr Ile Pro His Val Leu Phe Asn Trp
65                  70                  75                  80

Asn Phe Gly Ser Gly Ile Cys Met Phe Trp Leu Ile Thr Asp Tyr Leu
                85                  90                  95

Leu Cys Thr Ala Ser Val Tyr Asn Ile Val Leu Ile Ser Tyr Asp Arg
            100                 105                 110

Tyr Gln Ser Val Ser Asn Ala Val Ser Tyr Arg Ala Gln His Thr Gly
        115                 120                 125

Ile Met Lys Ile Val Ala Gln Met Val Ala Val Trp Ile Leu Ala Phe
    130                 135                 140

Leu Val Asn Gly Pro Met Ile Leu Ala Ser Asp Ser Trp Lys Asn Ser
145                 150                 155                 160

Thr Asn Thr Lys Asp Cys Glu Pro Gly Phe Val Thr Glu Trp Tyr Ile
                165                 170                 175

Leu Thr Ile Thr Met Leu Leu Glu Phe Leu Leu Pro Val Ile Ser Val
            180                 185                 190

Ala Tyr Phe Asn Val Gln Ile Tyr Trp Ser Leu Trp Lys Arg Arg Ala
        195                 200                 205

Leu Ser Arg Cys Pro Ser His Ala Gly Phe Ser Thr Thr Ser Ser Ser
    210                 215                 220

Ala Ser Gly His Leu His Arg Ala Gly Val Ala Cys Arg Thr Ser Asn
225                 230                 235                 240

Pro Gly Leu Lys Glu Ser Ala Ala Ser Arg His Ser Glu Ser Pro Arg
                245                 250                 255

Arg Lys Ser Ser Ile Leu Val Ser Leu Arg Thr His Met Asn Ser Ser
            260                 265                 270

Ile Thr Ala Phe Lys Val Gly Ser Phe Trp Arg Ser Glu Ser Ala Ala
        275                 280                 285

Leu Arg Gln Arg Glu Tyr Ala Glu Leu Leu Arg Gly Arg Lys Leu Ala
    290                 295                 300
```

-continued

```
Arg Ser Leu Ala Ile Leu Leu Ser Ala Phe Ala Ile Cys Trp Ala Pro
305                 310                 315                 320

Tyr Cys Leu Phe Thr Ile Val Leu Ser Thr Tyr Pro Arg Thr Glu Arg
                325                 330                 335

Pro Lys Ser Val Trp Tyr Ser Ile Ala Phe Trp Leu Gln Trp Phe Asn
            340                 345                 350

Ser Phe Val Asn Pro Phe Leu Tyr Pro Leu Cys His Arg Arg Phe Gln
        355                 360                 365

Lys Ala Phe Trp Lys Ile Leu Cys Val Thr Lys Trp Pro Ala Leu Ser
    370                 375                 380

Gln Asn Gln Ser Val Ser Ser
385                 390


<210> SEQ ID NO 9
<211> LENGTH: 391
<212> TYPE: PRT
<213> ORGANISM: Rattus rattus

<400> SEQUENCE: 9

Met Ser Glu Ser Asn Gly Thr Asp Val Leu Pro Leu Thr Ala Gln Val
1               5                   10                  15

Pro Leu Ala Phe Leu Met Ser Leu Leu Ala Phe Ala Ile Thr Ile Gly
            20                  25                  30

Asn Ala Val Val Ile Leu Ala Phe Val Ala Asp Arg Asn Leu Arg His
        35                  40                  45

Arg Ser Asn Tyr Phe Phe Leu Asn Leu Ala Ile Ser Asp Phe Phe Val
    50                  55                  60

Gly Val Ile Ser Ile Pro Leu Tyr Ile Pro His Thr Leu Phe Asn Trp
65                  70                  75                  80

Asn Pro Gly Ser Gly Ile Cys Met Phe Trp Leu Ile Thr Asp Tyr Leu
                85                  90                  95

Leu Cys Thr Ala Ser Val Tyr Ser Ile Val Leu Ile Ser Tyr Asp Arg
            100                 105                 110

Tyr Gln Ser Val Ser Asn Ala Val Arg Tyr Arg Ala Gln His Thr Gly
        115                 120                 125

Ile Leu Lys Ile Val Ala Gln Met Val Ala Val Trp Ile Leu Ala Phe
    130                 135                 140

Leu Val Asn Gly Pro Met Ile Leu Ala Ser Asp Ser Trp Lys Asn Ser
145                 150                 155                 160

Thr Asn Thr Glu Glu Cys Glu Pro Gly Phe Val Thr Glu Trp Tyr Ile
                165                 170                 175

Leu Ala Ile Thr Ala Phe Leu Glu Phe Leu Leu Pro Val Ser Leu Val
            180                 185                 190

Val Tyr Phe Ser Val Gln Ile Tyr Trp Ser Leu Trp Lys Arg Gly Ser
        195                 200                 205

Leu Ser Arg Cys Pro Ser His Ala Gly Phe Ile Ala Thr Ser Ser Arg
    210                 215                 220

Gly Thr Gly His Ser Arg Arg Thr Gly Leu Ala Cys Arg Thr Ser Leu
225                 230                 235                 240

Pro Gly Leu Lys Glu Pro Ala Ala Ser Leu His Ser Glu Ser Pro Arg
                245                 250                 255

Gly Lys Ser Ser Leu Leu Val Ser Leu Arg Thr His Met Ser Gly Ser
            260                 265                 270

Ile Ile Ala Phe Lys Val Gly Ser Phe Cys Arg Ser Glu Ser Pro Val
```

-continued

```
        275                 280                 285

Leu His Gln Arg Glu His Val Glu Leu Leu Arg Gly Arg Lys Leu Ala
    290                 295                 300

Arg Ser Leu Ala Val Leu Leu Ser Ala Phe Ala Ile Cys Trp Ala Pro
305                 310                 315                 320

Tyr Cys Leu Phe Thr Ile Val Leu Ser Thr Tyr Arg Arg Gly Glu Arg
                325                 330                 335

Pro Lys Ser Ile Trp Tyr Ser Ile Ala Phe Trp Leu Gln Trp Phe Asn
            340                 345                 350

Ser Leu Ile Asn Pro Phe Leu Tyr Pro Leu Cys His Arg Arg Phe Gln
        355                 360                 365

Lys Ala Phe Trp Lys Ile Leu Cys Val Thr Lys Gln Pro Ala Pro Ser
    370                 375                 380

Gln Thr Gln Ser Val Ser Ser
385                 390


<210> SEQ ID NO 10
<211> LENGTH: 389
<212> TYPE: PRT
<213> ORGANISM: Cavia porcellus

<400> SEQUENCE: 10

Met Leu Ala Asn Asn Ser Thr Ile Ala Leu Thr Ser Ile Lys Ile Ser
1               5                   10                  15

Leu Thr Phe Leu Met Ser Leu Leu Ala Ile Ala Ile Met Leu Gly Asn
            20                  25                  30

Val Val Val Ile Leu Ala Phe Ile Val Asp Arg Asn Leu Arg His Arg
        35                  40                  45

Ser Asn Tyr Phe Phe Leu Asn Leu Ala Ile Ala Asp Phe Phe Val Gly
    50                  55                  60

Ala Ile Ala Ile Pro Leu Tyr Ile Pro Ser Ser Leu Thr Tyr Trp Thr
65                  70                  75                  80

Ser Gly Lys Gln Ala Cys Val Phe Trp Leu Ile Thr Asp Tyr Leu Leu
                85                  90                  95

Cys Thr Ala Ser Val Tyr Asn Ile Val Leu Ile Ser Tyr Asp Arg Tyr
            100                 105                 110

Gln Ser Val Ser Asn Ala Val Trp Tyr Arg Ala Gln His Ser Gly Thr
        115                 120                 125

Trp Lys Ile Ala Thr Gln Met Val Ala Val Trp Ile Phe Ser Phe Met
    130                 135                 140

Thr Asn Gly Pro Met Ile Leu Ile Ser Asp Ser Trp Gln Asn Ser Thr
145                 150                 155                 160

Thr Glu Cys Glu Pro Gly Phe Leu Lys Lys Trp Tyr Phe Ala Leu Pro
                165                 170                 175

Thr Ser Leu Leu Glu Phe Leu Ile Pro Ile Leu Leu Val Ala Tyr Phe
            180                 185                 190

Ser Ala His Ile Tyr Trp Ser Leu Trp Lys Arg Glu Lys Leu Ser Arg
        195                 200                 205

Cys Leu Ser His Pro Val Leu Pro Ser Asp Ser Ser Ser Ser Asp His
    210                 215                 220

Gly His Ser Cys Arg Gln Asp Pro Asp Ser Arg Ala Thr Leu Pro Ala
225                 230                 235                 240

Arg Lys Glu Thr Thr Ala Ser Leu Gly Ser Asp Lys Ser Arg Arg Lys
                245                 250                 255
```

-continued

```
Ser Ser Leu Leu Pro Ser Ile Arg Ala Tyr Lys Asn Ser Asn Val Ile
            260                 265                 270

Ala Ser Lys Met Gly Phe Leu Ser His Ser Asp Ser Leu Ala Leu Gln
        275                 280                 285

Gln Arg Glu His Ile Glu Leu Phe Arg Ala Arg Lys Leu Ala Lys Ser
    290                 295                 300

Leu Ala Ile Leu Leu Ala Ala Phe Ala Ile Cys Trp Ala Pro Tyr Ser
305                 310                 315                 320

Leu Thr Thr Val Ile Tyr Ser Phe Phe Pro Glu Arg Asn Leu Thr Lys
                325                 330                 335

Ser Thr Trp Tyr His Thr Ala Phe Trp Leu Gln Trp Phe Asn Ser Phe
            340                 345                 350

Val Asn Pro Phe Leu Tyr Pro Leu Cys His Lys Arg Phe Gln Lys Ala
        355                 360                 365

Phe Leu Lys Ile Leu Pro Val Arg Arg Gln Ser Thr Pro Pro His Asn
    370                 375                 380

Arg Ser Ile Ser Thr
385


<210> SEQ ID NO 11
<211> LENGTH: 30
<212> TYPE: DNA
<213> ORGANISM: Artificial Sequence
<220> FEATURE:
<223> OTHER INFORMATION: Oligonucleotide Primer

<400> SEQUENCE: 11

gtggtggaca aaaaccttag acatcgaagt                                        30


<210> SEQ ID NO 12
<211> LENGTH: 30
<212> TYPE: DNA
<213> ORGANISM: Artificial Sequence
<220> FEATURE:
<223> OTHER INFORMATION: Oligonucleotide Primer

<400> SEQUENCE: 12

actgagatga tcacgcttcc acaggctcca                                        30


<210> SEQ ID NO 13
<211> LENGTH: 27
<212> TYPE: DNA
<213> ORGANISM: Artificial Sequence
<220> FEATURE:
<223> OTHER INFORMATION: Oligonucleotide Primer

<400> SEQUENCE: 13

ccatcctaat acgactcact atagggc                                           27


<210> SEQ ID NO 14
<211> LENGTH: 29
<212> TYPE: DNA
<213> ORGANISM: Artificial Sequence
<220> FEATURE:
<223> OTHER INFORMATION: Oligonucleotide Primer

<400> SEQUENCE: 14

cactctgtaa caaagccagg ctcacagtc                                         29


<210> SEQ ID NO 15
<211> LENGTH: 30
<212> TYPE: DNA
```

-continued

<213> ORGANISM: Artificial Sequence
<220> FEATURE:
<223> OTHER INFORMATION: Oligonucleotide Primer

<400> SEQUENCE: 15
tgcatctcgt cactcagaaa gtcctcgaag 30

<210> SEQ ID NO 16
<211> LENGTH: 39
<212> TYPE: DNA
<213> ORGANISM: Artificial Sequence
<220> FEATURE:
<223> OTHER INFORMATION: Oligonucleotide Primer

<400> SEQUENCE: 16
acgagaattc gccaccatgt cggagtctaa cagtactgg 39

<210> SEQ ID NO 17
<211> LENGTH: 39
<212> TYPE: DNA
<213> ORGANISM: Artificial Sequence
<220> FEATURE:
<223> OTHER INFORMATION: Oligonucleotide Primer

<400> SEQUENCE: 17
atgacagcgg ccgcagttgg cactcgtgaa gcaattctc 39

<210> SEQ ID NO 18
<211> LENGTH: 31
<212> TYPE: DNA
<213> ORGANISM: Artificial Sequence
<220> FEATURE:
<223> OTHER INFORMATION: Oligonucleotide Primer

<400> SEQUENCE: 18
cattgggcca ttgaccaaga aagccagtat c 31

<210> SEQ ID NO 19
<211> LENGTH: 30
<212> TYPE: DNA
<213> ORGANISM: Artificial Sequence
<220> FEATURE:
<223> OTHER INFORMATION: Oligonucleotide Primer

<400> SEQUENCE: 19
tcattcagaa agtccacgag gaaagagcag 30

<210> SEQ ID NO 20
<211> LENGTH: 39
<212> TYPE: DNA
<213> ORGANISM: Artificial Sequence
<220> FEATURE:
<223> OTHER INFORMATION: Oligonucleotide Primer

<400> SEQUENCE: 20
acgtgaattc gccaccatgt cggagtctaa cggcactga 39

<210> SEQ ID NO 21
<211> LENGTH: 39
<212> TYPE: DNA
<213> ORGANISM: Artificial Sequence
<220> FEATURE:
<223> OTHER INFORMATION: Oligonucleotide Primer

<400> SEQUENCE: 21
actgatgcgg ccgcgaagct ggcacacatg aagcttctc 39

-continued

<210> SEQ ID NO 22
<211> LENGTH: 30
<212> TYPE: DNA
<213> ORGANISM: Artificial Sequence
<220> FEATURE:
<223> OTHER INFORMATION: Oligonucleotide Primer

<400> SEQUENCE: 22
ataatgatgt agggagagca aagtaccact 30

<210> SEQ ID NO 23
<211> LENGTH: 30
<212> TYPE: DNA
<213> ORGANISM: Artificial Sequence
<220> FEATURE:
<223> OTHER INFORMATION: Oligonucleotide Primer

<400> SEQUENCE: 23
acactcctgc agacaggacc ccgattcaag 30

<210> SEQ ID NO 24
<211> LENGTH: 41
<212> TYPE: DNA
<213> ORGANISM: Artificial Sequence
<220> FEATURE:
<223> OTHER INFORMATION: Oligonucleotide Primer

<400> SEQUENCE: 24
acgtctcgag gccaccatgt tggcaaataa cagtacaatc g 41

<210> SEQ ID NO 25
<211> LENGTH: 41
<212> TYPE: DNA
<213> ORGANISM: Artificial Sequence
<220> FEATURE:
<223> OTHER INFORMATION: Oligonucleotide Primer

<400> SEQUENCE: 25
acgacagcgg ccgccttcaa gtggatattg agcggttgtg t 41

<210> SEQ ID NO 26
<211> LENGTH: 37
<212> TYPE: DNA
<213> ORGANISM: Artificial Sequence
<220> FEATURE:
<223> OTHER INFORMATION: Oligonucleotide Primer

<400> SEQUENCE: 26
actagaattc accgtgatgc cagatactaa tagcaca 37

<210> SEQ ID NO 27
<211> LENGTH: 33
<212> TYPE: DNA
<213> ORGANISM: Artificial Sequence
<220> FEATURE:
<223> OTHER INFORMATION: Oligonucleotide Primer

<400> SEQUENCE: 27
atgcaggatc cagcatttga gactgacagg tat 33